(12) United States Patent
Banet et al.

(10) Patent No.: US 9,259,183 B2
(45) Date of Patent: Feb. 16, 2016

(54) BODY-WORN SENSOR FOR CHARACTERIZING PATIENTS WITH HEART FAILURE

(71) Applicant: TOSENSE, INC., La Jolla, CA (US)

(72) Inventors: Matthew Banet, Kihei, HI (US); Susan Meeks Pede, Encinitas, CA (US); Marshal Singh Dhillon, San Diego, CA (US); Kenneth Robert Hunt, Vista, CA (US)

(73) Assignee: TOSENSE, INC., La Jolla, CA (US)

( * ) Notice: Subject to any disclaimer, the term of this patent is extended or adjusted under 35 U.S.C. 154(b) by 0 days.

(21) Appl. No.: 14/145,291

(22) Filed: Dec. 31, 2013

(65) Prior Publication Data

US 2014/0187976 A1    Jul. 3, 2014

Related U.S. Application Data

(60) Provisional application No. 61/747,864, filed on Dec. 31, 2012.

(51) Int. Cl.
| | |
|---|---|
| A61B 5/04 | (2006.01) |
| A61B 5/02 | (2006.01) |
| A61B 5/00 | (2006.01) |
| A61B 5/0205 | (2006.01) |
| A61B 5/0408 | (2006.01) |
| A61B 5/053 | (2006.01) |
| A61B 5/11 | (2006.01) |

(52) U.S. Cl.
CPC ............ *A61B 5/6822* (2013.01); *A61B 5/0205* (2013.01); *A61B 5/0408* (2013.01); *A61B 5/0531* (2013.01); *A61B 5/1117* (2013.01); *A61B 5/1118* (2013.01); *A61B 5/7225* (2013.01); *A61B 5/743* (2013.01)

(58) Field of Classification Search
USPC ......................................... 600/483, 508–509
See application file for complete search history.

(56) References Cited

U.S. PATENT DOCUMENTS

| | | | |
|---|---|---|---|
| 2011/0288605 A1* | 11/2011 | Kaib et al. ...................... 607/5 |
| 2012/0246795 A1* | 10/2012 | Scheffler et al. .................. 2/69 |
| 2014/0187974 A1 | 7/2014 | Banet et al. |

OTHER PUBLICATIONS

Bernstein, Impedance cardiography: Pulsatile blood flow and the biophysical and electrodynamic basis for the stroke volume equations. J Electr Bioimp; 2010;1:2-17.
Fuller, The validity of cardiac output measurement by thoracic impedance: a meta-analysis. Clin Invest Med. Apr. 1992;15(2):103-112.

\* cited by examiner

*Primary Examiner* — Nicole F Lavert
(74) *Attorney, Agent, or Firm* — Michael A. Whittaker

(57) ABSTRACT

The invention provides a sensor for measuring both impedance and ECG waveforms that is configured to be worn around a patient's neck. The sensor features 1) an ECG system that includes an analog ECG circuit, in electrical contact with at least two ECG electrodes, that generates an analog ECG waveform; and 2) an impedance system that includes an analog impedance circuit, in electrical contact with at least two (and typically four) impedance electrodes, that generates an analog impedance waveform. Also included in the neck-worn system are a digital processing system featuring a microprocessor, and an analog-to-digital converter. During a measurement, the digital processing system receives and processes the analog ECG and impedance waveforms to measure physiological information from the patient. Finally, a cable that drapes around the patient's neck connects the ECG system, impedance system, and digital processing system.

10 Claims, 19 Drawing Sheets

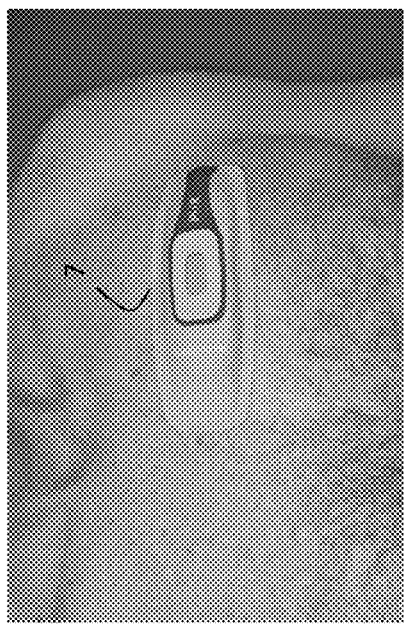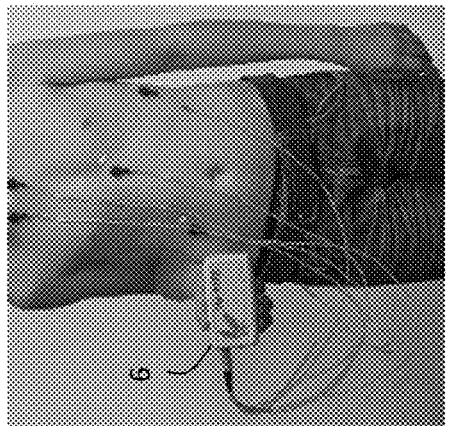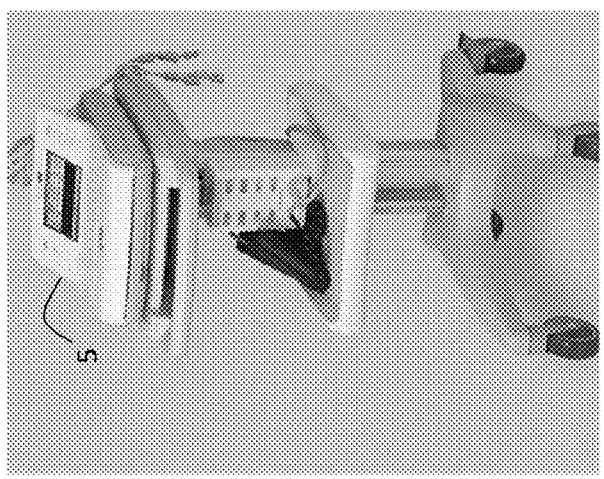
FIG. 4 PRIOR ART

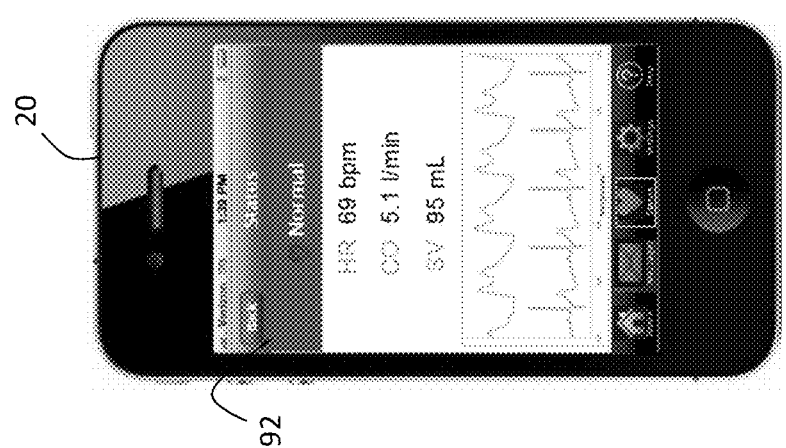
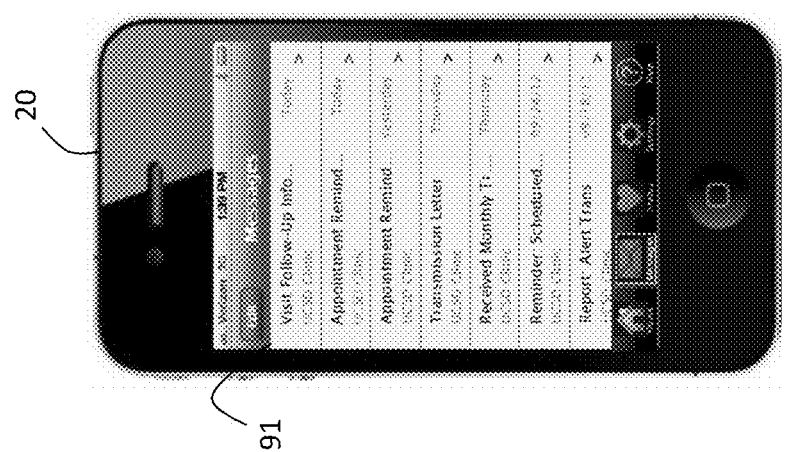
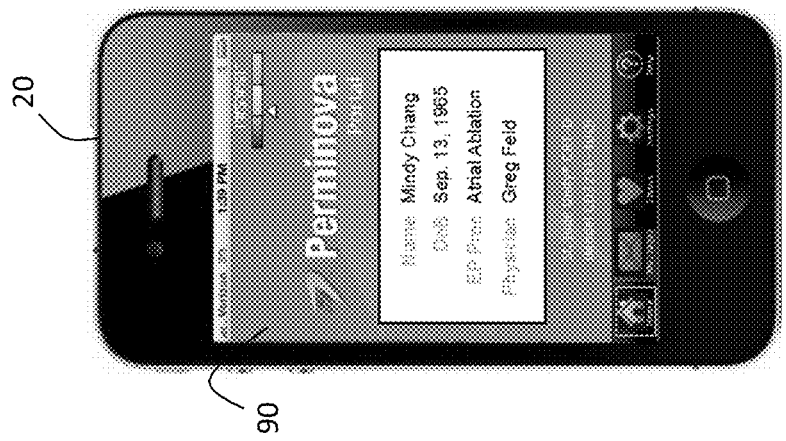
FIG. 10

BODY-WORN SENSOR FOR CHARACTERIZING PATIENTS WITH HEART FAILURE

CROSS REFERENCES TO RELATED APPLICATIONS

This application claims the benefit of U.S. Provisional Application No. 61/747,864, filed Dec. 31, 2012, which is hereby incorporated in its entirety including all tables, figures, and claims.

STATEMENT REGARDING FEDERALLY SPONSORED RESEARCH OR DEVELOPMENT

None.

BACKGROUND OF THE INVENTION

1. Field of the Invention

The present invention relates to sensors for characterizing patients suffering from congestive heart failure (CHF) and related diseases.

2. Description of the Related Art

CHF occurs when the heart is unable to sufficiently pump and distribute blood to meet the body's needs. CHF is typically preceded by an increase of fluid in the thoracic cavity, and can by characterized by shortness of breath, swelling of the legs and other appendages, and intolerance to exercise. It affects nearly 5.3 M Americans and has an accompanying cost of somewhere between $30-50 B, with roughly $17 B attributed to hospital readmissions. Such events are particularly expensive to hospitals, as readmissions occurring within a 30-day period are not reimbursable by Medicare or private insurance as of October 2012.

In medical centers, CHF is typically detected using Doppler/ultrasound, which measures parameters such as stroke volume (SV), cardiac output (CO), and ejection fraction (EF). Gradual weight gain measured with a simple scale is one method to indicate CHF in the home environment. However, this parameter is typically not sensitive enough to detect the early onset of CHF, a particularly important time when the condition may be ameliorated by a change in medication or diet.

SV is the mathematical difference between left ventricular end-diastolic volume (EDV) and end-systolic volume (ESV), and represents the volume of blood ejected by the left ventricle with each heartbeat; a typical value is about 80 mL. EF relates to EDV and ESV as described below in Eq. 1, with a typical value for healthy individuals being about 50-65%, and an ejection fraction of less than 40% indicating systolic heart failure.

$$EF = \frac{SV}{EDV} \qquad (1)$$
$$= \frac{EDV - ESV}{EDV}$$

CO is the average, time-dependent volume of blood ejected from the left ventricle into the aorta and, informally, indicates how efficiently a patient's heart pumps blood through their arterial tree; a typical value is about 5 L/min. CO is the product of HR and SV, i.e.:

$$CO = SV \times HR \qquad (2)$$

CHF patients, in particular those suffering from systolic heart failure, may receive implanted devices, such as pacemakers and/or implantable cardioverter-defibrillators, to increase EF and subsequent blood flow throughout the body. These devices also include technologies called 'OptiVol' (from Medtronic) or 'CorVue' (St. Jude) that use circuitry and algorithms within the implanted device to measure the electrical impedance between different leads of the pacemaker. As thoracic fluid increases in the CHF patient, the impedance typically is reduced. Thus this parameter, when read by an interrogating device placed outside the patient's body, can indicate the onset of heart failure.

Corventis Inc. has developed the AVIVO™ Mobile Patient Management (MPM) System to characterize ambulatory CHF patients. AVIVO™ is typically used over a 7-day period, during which it provides continual insight into a patient's physiological status by steadily collecting data and wirelessly transmitting it through a small handheld device to a central server for analysis and review. The system consists of three parts: 1) The PiiX™ sensor, a patient-worn adhesive device that resembles a large (approximately 15" long) bandage and measures fluid status, electrocardiography (ECG) waveforms, heart rate (HR), respiration rate, patient activity, and posture; 2) The zLink™ Mobile Transmitter, a small, handheld device that receives information from the Piix™ sensor and then transmits data wirelessly to a remote server via cellular technology; and 3) the Corventis Monitoring Center, where data are collected and analyzed. Technicians staff the Monitoring Center, review the incoming data, and in response generate clinical reports made available to prescribing physicians by way of a web-based user interface.

In some cases, physicians can prescribe ECG monitors to ambulatory CHF patients. These systems measure time-dependent waveforms, from which heart rate HR and information related to arrhythmias and other cardiac properties are extracted. They characterize ambulatory patients over short periods (e.g. 24-48 hours) using 'holier' monitors, or over longer periods (e.g. 1-3 weeks) using cardiac event monitors. Conventional holter or event monitors typically include a collection of chest-worn ECG electrodes (typically 3 or 5), an ECG circuit that collects analog signals from the ECG electrodes and converts these into multi-lead ECG waveforms; a processing unit then analyzes the ECG waveforms to determine cardiac information. Typically the patient wears the entire system on their body. Some modern ECG-monitoring systems include wireless capabilities that transmit ECG waveforms and other numerical data through a cellular interface to an Internet-based system, where they are further analyzed to generate, for example, reports describing the patient's cardiac rhythm. In less sophisticated systems, the ECG-monitoring system is worn by the patient, and then returned to a company that downloads all relevant information into a computer, which then analyzes it to generate the report. The report, for example, may be imported into the patient's electronic medical record (EMR). The EMR avails the report to cardiologists or other clinicians, who then use it to help characterize the patient.

Measuring CO and SV in a continuous, non-invasive manner with high clinical accuracy has often been considered a 'holy grail' of medical-device monitoring. Most existing techniques in this field require in-dwelling catheters, which in turn can lead to complications with the patient, are inherently inaccurate in the critically ill, and require a specially trained operator. For example, current 'gold standards' for this measurement are thermodilution cardiac output (TDCO) and the Fick Oxygen Principal (Fick). However both TDCO and Fick are highly invasive techniques that can cause infection and other complications, even in carefully controlled hospital environments. In TDCO, a pulmonary artery catheter (PAC), also known as a Swan-Ganz catheter, is typically inserted into the right portion of the patient's heart. Procedurally a bolus (typically 10 ml) of glucose or saline that is cooled to a known temperature is injected through the PAC. A temperature-measuring device within the PAC, located a known distance away (typically 6-10 cm) from where fluid is injected, measures the progressively increasing temperature of the diluted blood. CO is then estimated from a measured time-temperature curve, called the 'thermodilution curve'. The larger the area under this curve, the lower the cardiac output Likewise, the smaller the area under the curve implies a shorter transit time for the cold bolus to dissipate, hence a higher CO.

Fick involves calculating oxygen consumed and disseminated throughout the patient's blood over a given time period. An algorithm associated with the technique incorporates consumption of oxygen as measured with a spirometer with the difference in oxygen content of centralized blood measured from a PAC and oxygen content of peripheral arterial blood measured from an in-dwelling cannula.

Both TD and Fick typically measure CO with accuracies between about 0.5-1.0 l/min, or about +/−20% in the critically ill.

Several non-invasive techniques for measuring CO and SV have been developed with the hope of curing the deficiencies of Fick and TD. For example, Doppler-based ultrasonic echo (Doppler/ultrasound) measures blood velocity using the well-known Doppler shift, and has shown reasonable accuracy compared to more invasive methods. But both two and three-dimensional versions of this technique require a specially trained human operator, and are thus, with the exception of the esophageal Doppler technique, impractical for continuous measurements. CO and SV can also be measured with techniques that rely on electrodes placed on the patient's torso that inject and then collect a low-amperage, high-frequency modulated electrical current. These techniques, based on electrical bioimpedance and called 'impedance cardiography' (ICG), 'electrical cardiometry velocimetry' (ECV), and 'bioreactance' (BR), measure a time-dependent electrical waveform that is modulated by the flow of blood through the patient's thorax. Blood is a good electrical conductor, and when pumped by the heart can further modulate the current injected by these techniques in a manner sensitive to the patient's CO. During a measurement, ICG, ECV, and BR each extract properties called left ventricular ejection time (LVET) and pre-injection period (PEP) from time-dependent ICG and ECG waveforms. A processor then analyzes the waveform with an empirical mathematical equation, shown below in Eq. 3, to estimate SV. CO is then determined from the product of SV and HR, as described above in Eq. 2.

ICG, ECV, and BR all represent a continuous, non-invasive alternative for measuring CO/SV, and in theory can be conducted with an inexpensive system and no specially trained operator. But the medical community has not embraced such methods, despite the fact that clinical studies have shown them to be effective with some patient populations. In 1992, for example, an analysis by Fuller et al. analyzed data from 75 published studies describing the correlation between ICG and TD/Fick (Fuller et al., *The validity of cardiac output measurement by thoracic impedance: a meta-analysis*; Clinical Investigative Medicine; 15: 103-112 (1992)). The study concluded using a meta analysis wherein, in 28 of these trials, ICG displayed a correlation of between r=0.80-0.83 against TDCO, dye dilution and Fick CO. Patients classified as critically ill, e.g. those suffering from acute myocardial infarction, sepsis, and excessive lung fluids, yielded worse results.

Further impeding commercial acceptance of these techniques is the tendency of ICG monitors to be relatively bulky and similar in both size and complexity to conventional vital signs monitors. This means two large and expensive pieces of monitoring equipment may need to be located bedside in order to monitor a patient's vital signs and CO/SV. For this and other reasons, impedance-based measurements of CO have not achieved widespread commercial success.

SUMMARY OF THE INVENTION

The current invention provides a simple, low-cost, non-invasive sensor that measures CO, SV, fluid levels, ECG waveforms, HR, arrhythmias, temperature, location, and motion/posture/activity level from CHF and other patients. The sensor, which is shaped like a conventional necklace, is particularly designed for ambulatory patients: with this form factor, it can be easily draped around a patient's neck, where it then makes the above-described measurements during the patient's day-to-day activities. Using a short-range wireless radio, the sensor transmits data to the patient's cellular telephone, which then processes and retransmits the data over cellular networks to a web-based system. The web-based system generates reports for supervising clinicians, who can then adjust the patient's diet, exercise, and medication regime to prevent the onset of CHF.

The sensor features a miniaturized impedance-measuring system, described in detail below, that is built into the necklace form factor. This system measures a time-dependent, transbrachial impedance (TBI) waveform that is then processed to determine CO, SV, and fluid levels, as described in detail below. Accompanying this system is a collection of algorithms that perform signal processing and account for the patient's motion, posture and activity level, as measured with an internal accelerometer, to improve the calculations for all hemodynamic measurements. Compensation of motion is particularly important since measurements are typically made from ambulatory patients. Also within the necklace is a medical-grade ECG system that measures single-lead ECG waveform and accompanying values of HR and cardiac arrhythmias. The system also analyzes other components of the ECG waveforms, which include: i) a QRS complex; ii) a P-wave; iii) a T-wave; iv) a U-wave; v) a PR interval; vi) a QRS interval; vii) a QT interval; viii) a PR segment; and ix) an ST segment. The temporal or amplitude-related features of these components may vary over time, and thus the algorithmic-based tools within the system, or software associated with the algorithm-based tools, can analyze the time-dependent evolution of each of these components. In particular, algorithmic-based tools that perform numerical fitting, mathematical modeling, or pattern recognition may be deployed to determine the components and their temporal and amplitude characteristics for any given heartbeat recorded by the system.

As an example, physiological waveforms measured with the sensor may be numerically 'fit' with complex mathematical functions, such as multi-order polynomial functions or pre-determined, exemplary waveforms. These functions may then be analyzed to determine the specific components, or changes in these components, within the waveform. In related embodiments, waveforms may be analyzed with more complex mathematical models that attempt to associate features of the waveforms with specific bioelectric events associated with the patient.

Each of the above-mentioned components corresponds to a different feature of the patient's cardiac system, and thus analysis of them according to the invention may determine or predict the onset of CHF.

Other conditions that can be determined through analysis of ECG waveforms include: blockage of arteries feeding the heart (each related to the PR interval); aberrant ventricular activity or cardiac rhythms with a ventricular focus (each related to the QRS interval); prolonged time to cardiac repolarization and the onset of ventricular dysrhythmias (each related to the QT interval); P-mitrale and P-pulmonale (each related to the P-wave); hyperkalemia, myocardial injury, myocardial ischemia, myocardial infarction, pericarditis, ventricular enlargement, bundle branch block, and subarachnoid hemorrhage (each related to the T-wave); and bradycardia, hypokalemia, cardiomyopathy, and enlargement of the left ventricle (each related to the U-wave). These are only a small subset of the cardiac conditions that may be determined or estimated through analysis of the ECG waveform according to the invention.

In one aspect, the invention provides a sensor for measuring both impedance and ECG waveforms that is configured to be worn around a patient's neck. The sensor includes: 1) an ECG system featuring an analog ECG circuit, in electrical contact with at least two ECG electrodes, that generates an analog ECG waveform; and 2) an impedance system featuring an analog impedance circuit, in electrical contact with at least two (and typically four) impedance electrodes, that generates an analog impedance waveform. Also included in the neck-worn system are a digital processing system featuring a microprocessor, and an analog-to-digital converter. During a measurement, the digital processing system receives and processes the analog ECG and impedance waveforms to measure physiological information from the patient. Finally, a cable that drapes around the patient's neck electrically and mechanically connects the ECG system, impedance system, and digital processing system.

In embodiments, the cable features a plurality of conducting wires that connect the ECG and impedance systems to the digital processing system. For example, the sensor may include a flexible circuit made from a tape-like material such as Kapton. In embodiments, the system features at least two non-flexible circuit boards, connected to each other with the flexible circuit, to form a 'sensor necklace'. Typically the necklace includes multiple, alternative flexible and non-flexible systems. Circuitry for the ECG, impedance, and digital processing systems is typically located on the non-flexible circuit boards.

In other embodiments, the cable includes a first ECG electrode in a first segment of the necklace that contacts a first side of the patient's chest, and a second ECG electrode in a second segment that contacts a second, opposing side of the patient's chest. For the impedance measurement, the cable also includes first and second impedance electrodes in, respectively, the first and second segments of the necklace. These electrodes are opposing sides of the patient's chest to make the impedance measurements.

In preferred embodiments, the impedance system features four distinct electrodes, i.e. a first current-injecting electrode, a second current-injecting electrode, a first voltage-measuring electrode, and a second voltage-measuring electrode. Here, the cable features a first segment that includes a first ECG electrode, the first current-injecting electrode, and the first voltage-measuring electrode, and a second segment that includes a second ECG electrode, the second current-injecting electrode, and the second voltage-measuring electrode. As before, the first and second segments are configured to contact opposing sides of the patient's chest.

A battery system powers the ECG, the impedance, and the digital processing systems. To complement the necklace design, the cable used to connect these systems also includes the battery system. More specifically, the cable includes a first connector and the battery system includes a second connector, with the first connector mated to the second connector so that the battery system can be detachable removed. The cable can also include a wireless transceiver based on a protocol such as Bluetooth and/or 802.11-based transceiver, as well as a USB connector in electrical contact with a flash memory system.

In another aspect, the invention provides a method for monitoring an electrical impedance from a patient. The method comprising the following steps: 1) providing a loop-shaped, flexible member, configured to be positioned around the patient's neck, that includes: i) at least four electrodes, each connected to the flexible member, where a first set of electrodes injects electrical current into the patient near their neck, and a second set of electrodes measures electrical signals from the patient; ii) an impedance-measuring system within the flexible member and in electrical contact with the second set of electrodes; and iii) a data-processing system, also within the flexible member and in electrical contact with the impedance-measuring system; 2) injecting electrical current into the patient near their neck with at least one electrode in the first set of electrodes; 3) measuring a voltage with the second set of electrodes, where the voltage relates to a product of the injected current and an impedance of the patient; and 4) processing the voltage to determine an impedance value.

In embodiments, the method includes step of measuring a voltage with the second set of electrodes using a differential amplifier configured to measure a time-dependent voltage indicating the product of electrical impedance near the patient's chest and current injected by the second set of electrodes. The time-dependent voltage can indicate how fluid levels and respiration affect electrical impedance in the patient's chest, and can thus be used to estimate these parameters. In other embodiments, the differential amplifier generates a time-dependent voltage that indicates how heartbeat-induced blood flow affects electrical impedance in the patient's chest. Here, the method includes processing the time-dependent voltage with a computer algorithm to estimate the patient's SV, CO, and/or HR, with the equations central to these algorithms described below in Eqs. 1-4. The method can also include the step of measuring an ECG waveform with an ECG system, the ECG system being embedded within the loop-shaped, flexible member. Here, the method processes the ECG waveform to determine HR, arrhythmias, HR variability, and other cardiac properties. In all cases, the method includes the step of wirelessly transmitting information to an external computer, such as a central monitoring station in a hospital, or a cellular telephone.

In another aspect, the invention provides a method for generating an alarm indicating fluid build-up for a patient using the sensor and methods described herein. Here, the method uses a computer algorithm to estimate the fluid levels in the patient's chest, and then compares trends in these values, or related values such as impedance or voltage measured with the sensor, to one or more pre-determined values. The method generates an alarm when one or more impedance values in the trend in impedance values, or a slope in these values, exceeds the pre-determined value. In related embodiments, the alarm is only generated when the parameter of interest exceeds the pre-determined value for a pre-determined period of time. When the alarm is generated, the method transmits it to the central monitoring station, cellular telephone, or other device. In general, alarms can be generated using any parameter measured by the sensor described herein, e.g. SV, CO, HR, or motion/posture/activity level.

The invention has many advantages. In general, it combines a comfortable sensor system with a web-based software system that, working in concert, allow a clinician to monitor a robust set of cardiovascular parameters from a CHF patient. The cardiovascular parameters feature those associated with the heart's mechanical properties (i.e. CO and SV) and electrical properties (i.e. HR and ECG). Taken collectively, these give the clinician a unique insight into the patient's condition.

These and other advantages will be apparent from the following detailed description, and from the claims.

BRIEF DESCRIPTION OF THE DRAWINGS

FIG. 4 shows photographs of systems described in the prior art that use impedance measurements to monitor a patient;

FIG. 10 shows screen captures from a software application operating on the cellular telephone of FIG. 9;

DETAILED DESCRIPTION OF THE INVENTION

Figure 1:
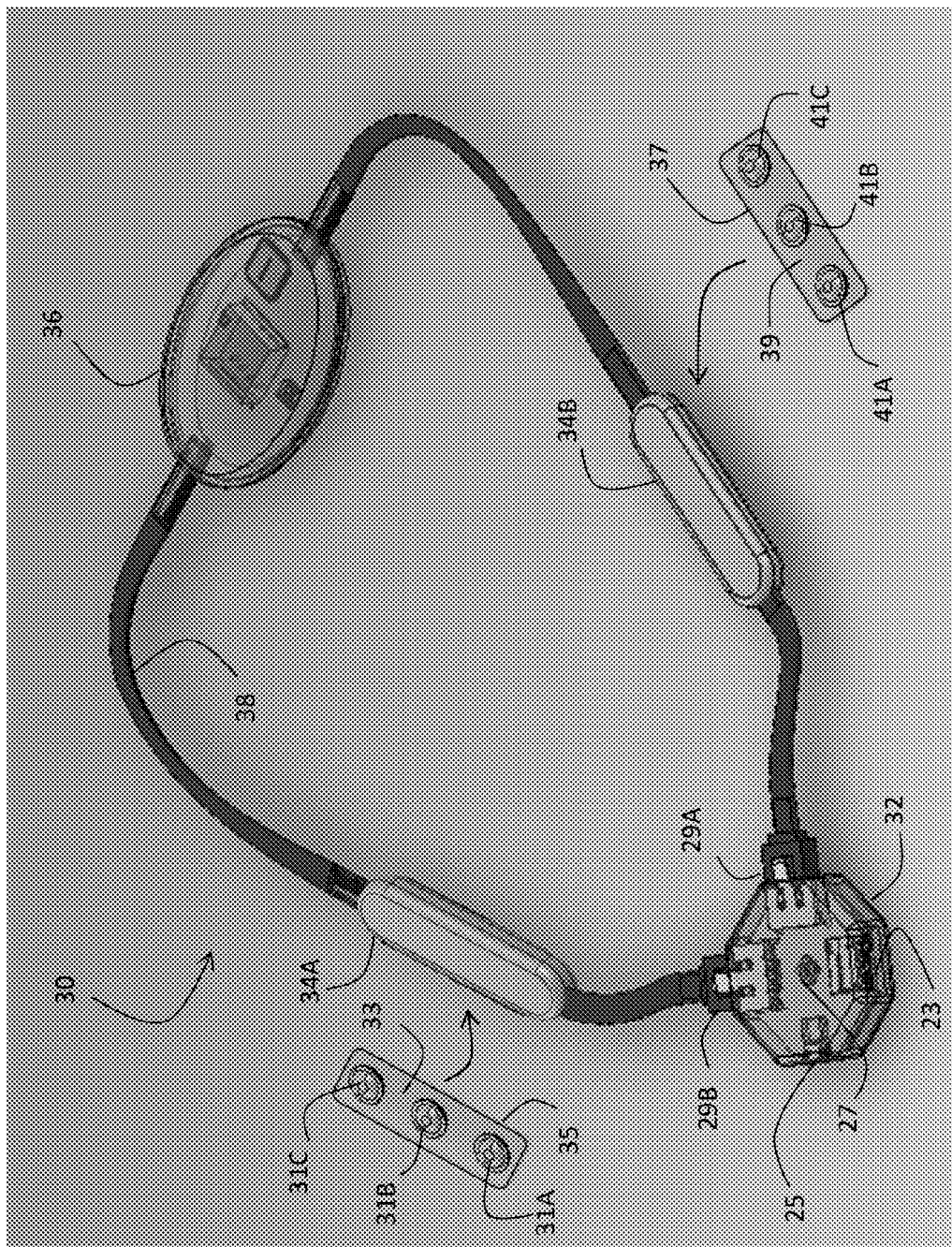
FIG. 1 shows a three-dimensional image of a necklace-shaped sensor that measures CO, SV, fluid levels, ECG waveforms, HR, arrhythmias, and motion/posture/activity level from an ambulatory patient.
Figure 2:
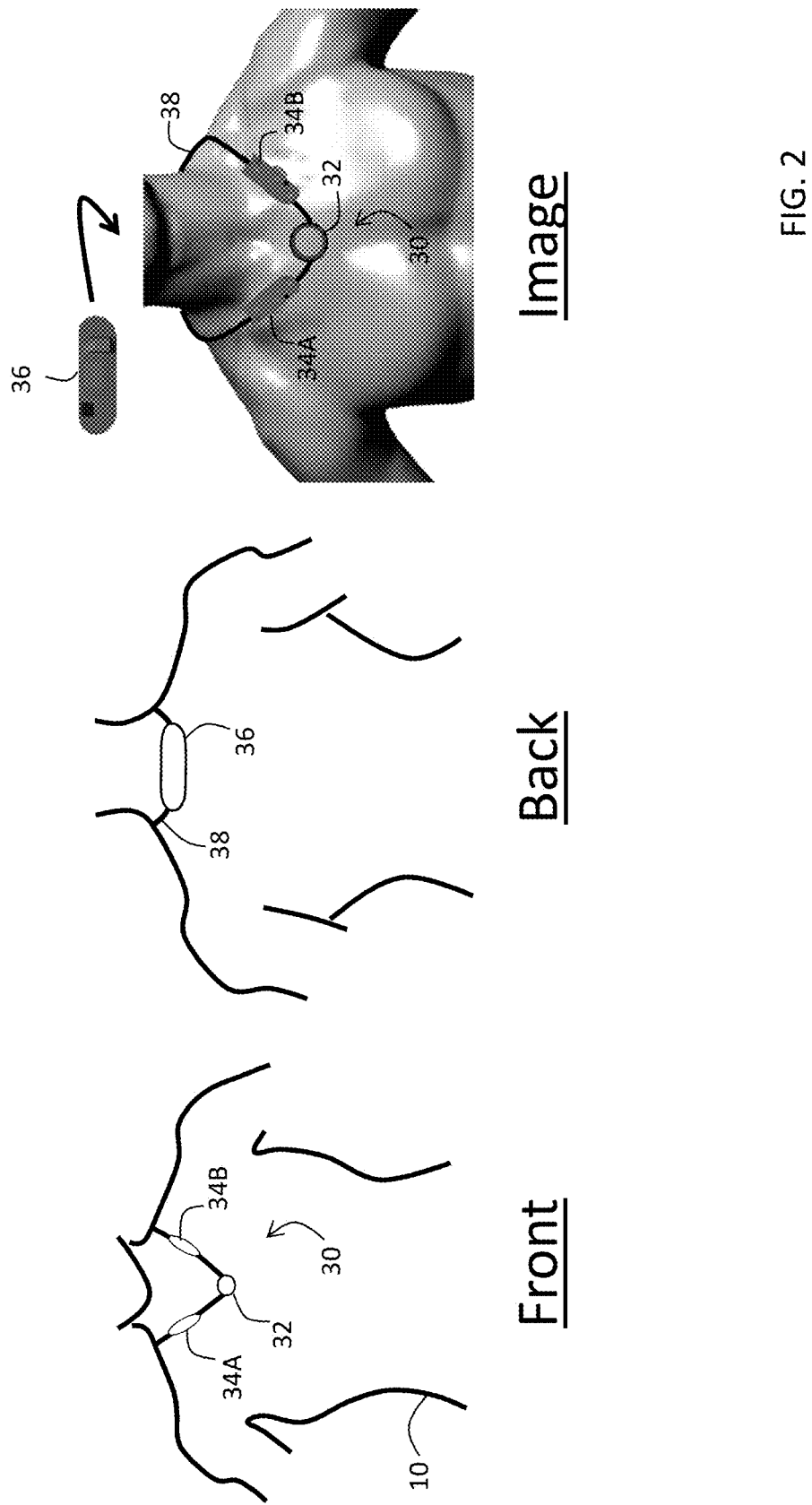
FIG. 2 shows two and three-dimensional images of the sensor of FIG. 1 worn around a patient's neck.

As shown in FIGS. 1 and 2, the invention provides a physiological sensor 30 that, during use, is comfortably worn around the patient's neck like a conventional necklace. The sensor 30 is designed for patients suffering from CHF and other cardiac diseases, such as cardiac arrhythmias, as well as patients with implanted devices such as pacemakers and ICDs. It makes impedance measurements to determine CO, SV, and fluid levels, and ECG measurements to determine a time-dependent ECG waveform and HR. Additionally it measures respiratory rate, skin temperature, location, and motion-related properties such as posture, activity level, falls, and degree of motion. The sensor's form factor is designed for both one-time measurements, which take just a few minutes, and continuous measurements, which can take several days. Necklaces are likely familiar to a patient 10 wearing the sensor 30, and this in turn may improve their compliance in making measurements as directed by their physician. Ultimately compliance in using the sensor may improve the patient's physiological condition. Moreover, the sensor is designed to make measurements near the center of the chest, which is relatively insensitive to motion compared to distal extremities, like the arms or hands. The sensor's form factor also ensures relatively consistent electrode placement for the impedance and ECG measurements; this is important for one-time measurements made on a daily basis, as it minimizes day-to-day errors associated with electrode placement. Finally, the sensor's form factor distributes electronics around the patient's neck, thereby minimizing bulk and clutter associated with these components and making the sensor 30 more comfortable to the patient.

Figure 5:
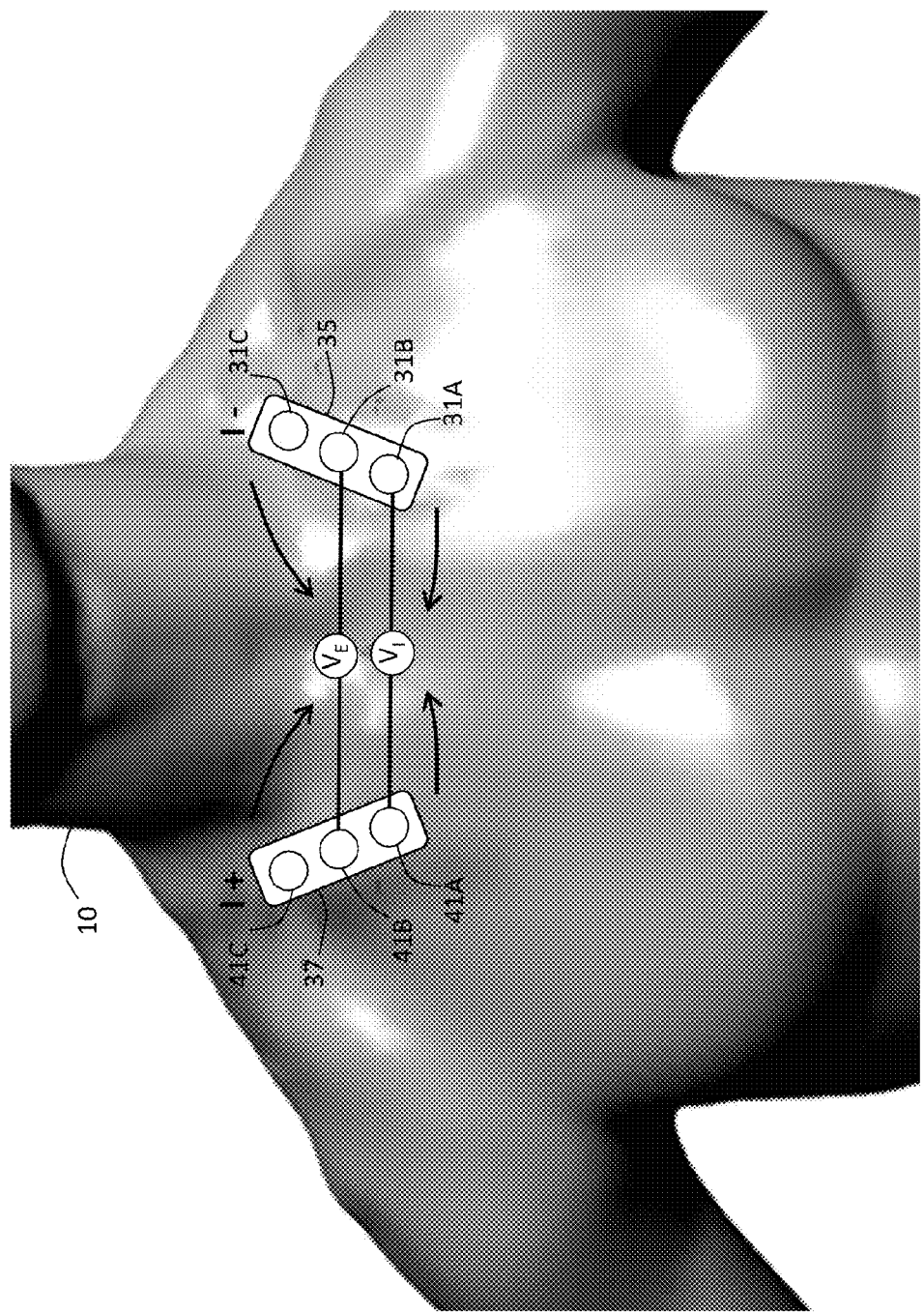
FIG. 5 shows a schematic drawing of electrodes used for the ECG and impedance systems positioned on the patient's chest using the sensor of FIGS. 1 and 3.
Figure 6:
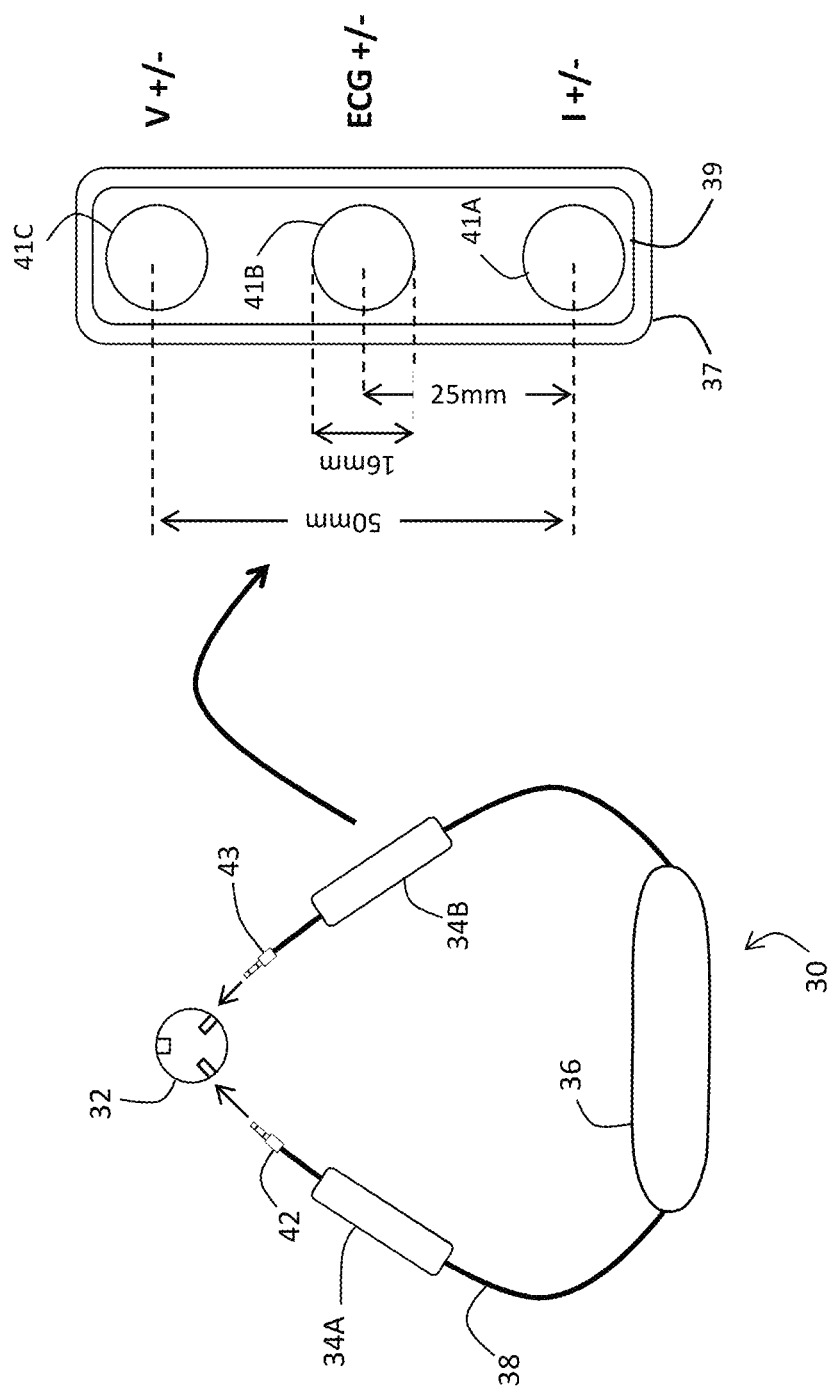
FIG. 6 shows a mechanical drawing of the sensor of FIG. 1 and its associated electrodes for ECG and impedance measurements.
Figure 7:
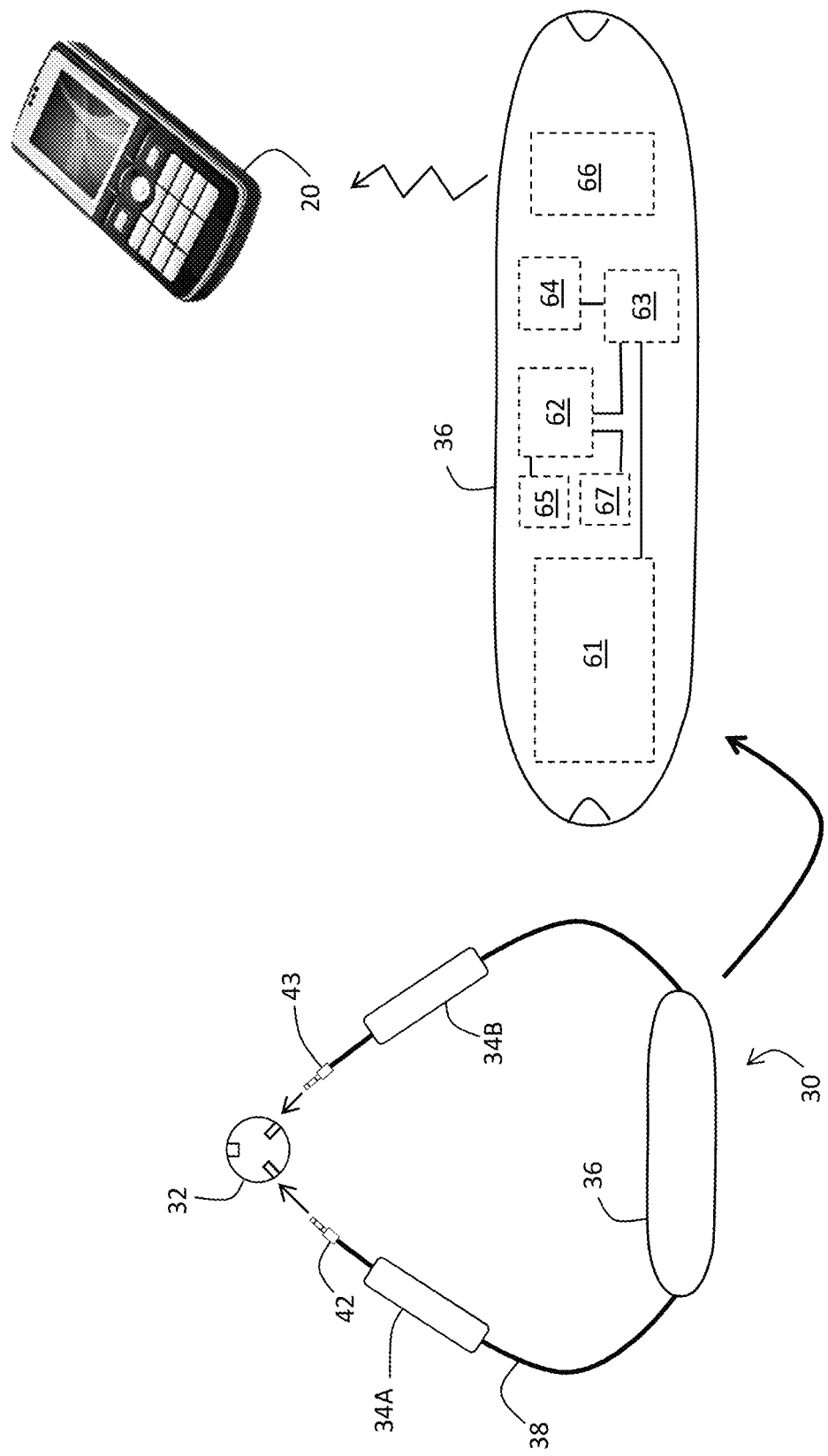
FIG. 7 shows a mechanical drawing of the sensor of FIG. 1 and its associated electronics for ECG, impedance, and digital processing systems.

In one embodiment the sensor 30 features a pair of electrode holders 34A, 34B, located on opposing sides of the necklace, that each receive a separate 3-part electrode patch 35, 37, shown in more detail in FIG. 6. During use, the electrode patches 35, 37 snap into their respective electrode holders 34A, 34B, and then stick to the patient's chest when the sensor 30 is draped around their neck. An adhesive backing 33, 39 supports each conductive electrode 31A-C, 41A-C within the electrode patch 35, 37. The electrodes 31A-C, 41A-C feature a sticky, conductive gel that contacts the patient's skin. The conductive gel contacts a metal rivet that is coated on one side with a thin layer of Ag/AgCl, and is designed to snap into a mated connector within the electrode holders 34A, 34B. As shown in more detail in FIG. 5, the outer electrodes 31A, 31C, 41A, 41C in each electrode patch are used for the impedance measurement (they conduct signals V+/−, I+/−), while the inner electrodes 31B, 41B are used for the ECG measurement (they conduct signals ECG+/−). Proper spacing of the electrodes 31A, 31C, 41A, 41C ensures both impedance and ECG waveforms having high signal-to-noise ratios; this in turn leads to measurements that are relatively easy to analyze, and thus have optimum accuracy. FIG. 6 shows preferred dimensions for these components.

A flexible, flat cable 38 featuring a collection of conductive members transmits signals from the electrode patches 35, 37 to an electronics module 36, which, during use, is preferably worn near the back of the neck. The electronic module 36 may snap into a soft covering to increase comfort. The electronics module 36, as described in detail below with reference to FIG.

7, features a first electrical circuit 61 for making an impedance-based measurement of TBI waveforms that yield CO, SV, and fluid levels, and a second electrical circuit 64 for making differential voltage measurements of ECG waveforms that yield HR and arrhythmia information. The first electrical circuit 61, which is relatively complex, is shown schematically in FIG. 11; the second electrical circuit 64 is well known in this particular art, and is thus not described in detail here.

During a measurement, the second electrical circuit 64 measures an analog ECG waveform that is received by an internal analog-to-digital converter within a microprocessor 62. The microprocessor analyzes this signal to simply determine that the electrode patches are properly adhered to the patient, and that the system is operating satisfactorily. Once this state is achieved, the first 61 and second 64 electrical circuits generate time-dependent analog waveforms that a high-resolution analog-to-digital converter 62 within the electronics module 36 receives and then sequentially digitizes to generate time-dependent digital waveforms. Analog waveforms can be switched over to this component, for example, using a field effect transistor (FET). Typically these waveforms are digitized with 16-bit resolution over a range of about −5V to 5V. The microprocessor 62 receives the digital waveforms and processes them with computational algorithms, written in embedded computer code (such as C or Java®) (Oracle, Inc.), to generate values of CO, SV, fluid level, and HR. An example of an algorithm is described with reference to FIG. 15. Additionally, the electronics module 36 features a 3-axis accelerometer 65 and temperature sensor 67 to measure, respectively, three time-dependent motion waveforms (along x, y, and z-axes) and temperature values. The microprocessor 62 analyzes the time-dependent motion waveforms to determine motion-related properties such as posture, activity level, falls, and degree of motion. Temperature values indicate the patient's skin temperature, and can be used to estimate their core temperature (a parameter familiar to physicians), as well as ancillary conditions, such as perfusion, ambient temperature, and skin impedance. Motion-related parameters are determined using techniques known in the art, and are described in more detail with reference to FIG. 12. Temperature values are preferably reported in digital form that the microprocessor receives through a standard serial interface, such as I2C, SPI, or UART.

Figure 9:
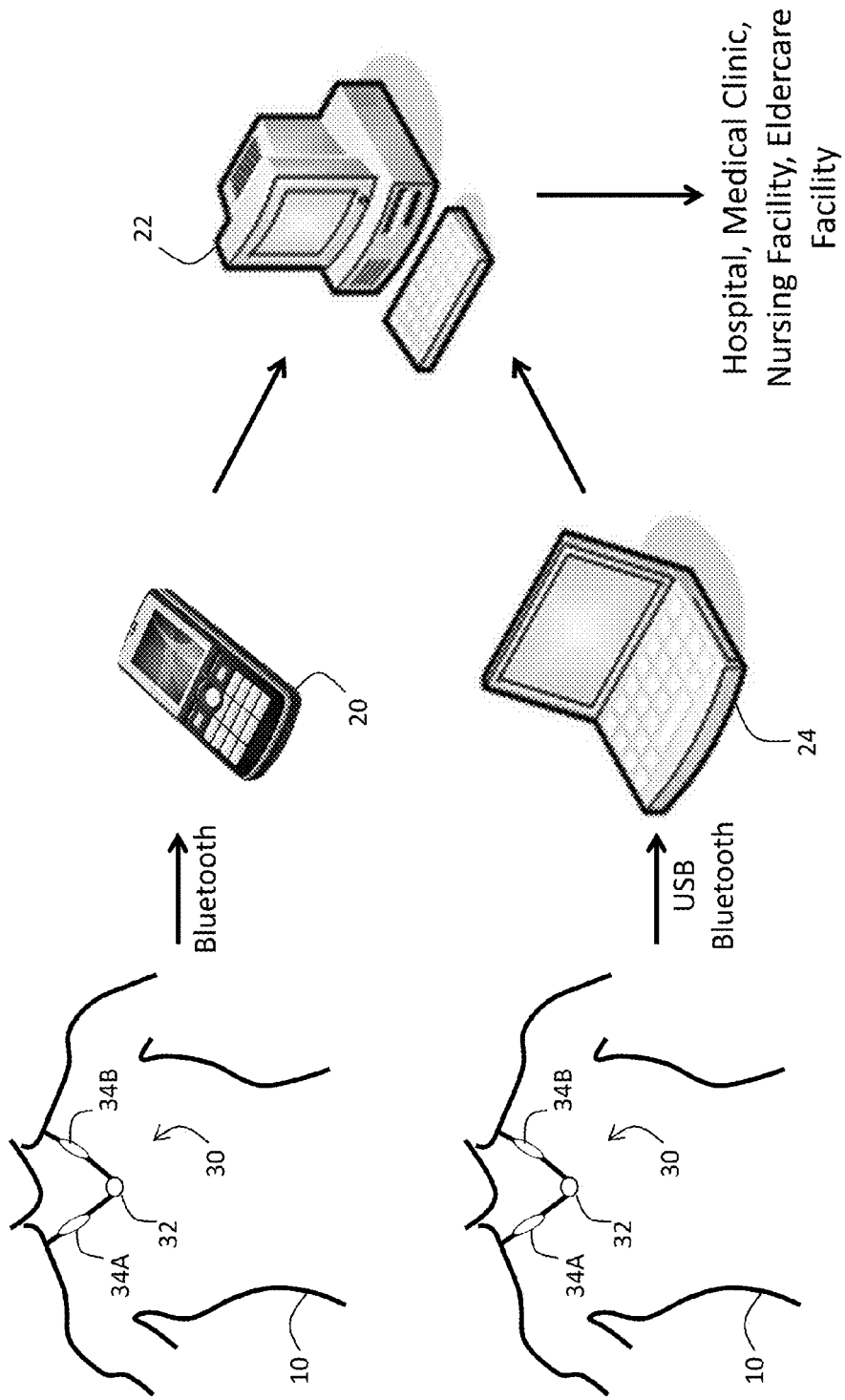
FIG. 9 shows a schematic drawing of the sensor of FIG. 1 transmitting data to a computer server using the patient's cellular telephone and/or personal computer.

Both numerical and waveform data processed with the microprocessor 62 are ported to a wireless transmitter 66 within the electronics module 36, such as a transmitter based on protocols like Bluetooth® (Bluetooth SIG, Inc.) or 802.11a/b/g/n. From there, the transmitter 66 sends data to an external receiver, such as a conventional cellular telephone 20, tablet, wireless hub (such as Qualcomm's 2Net™ system), or personal computer. Devices like these can serve as a 'hub' to forward data to an Internet-connected remote server located, e.g., in a hospital, medical clinic, nursing facility, or eldercare facility, as shown in FIG. 9.

Figure 8:
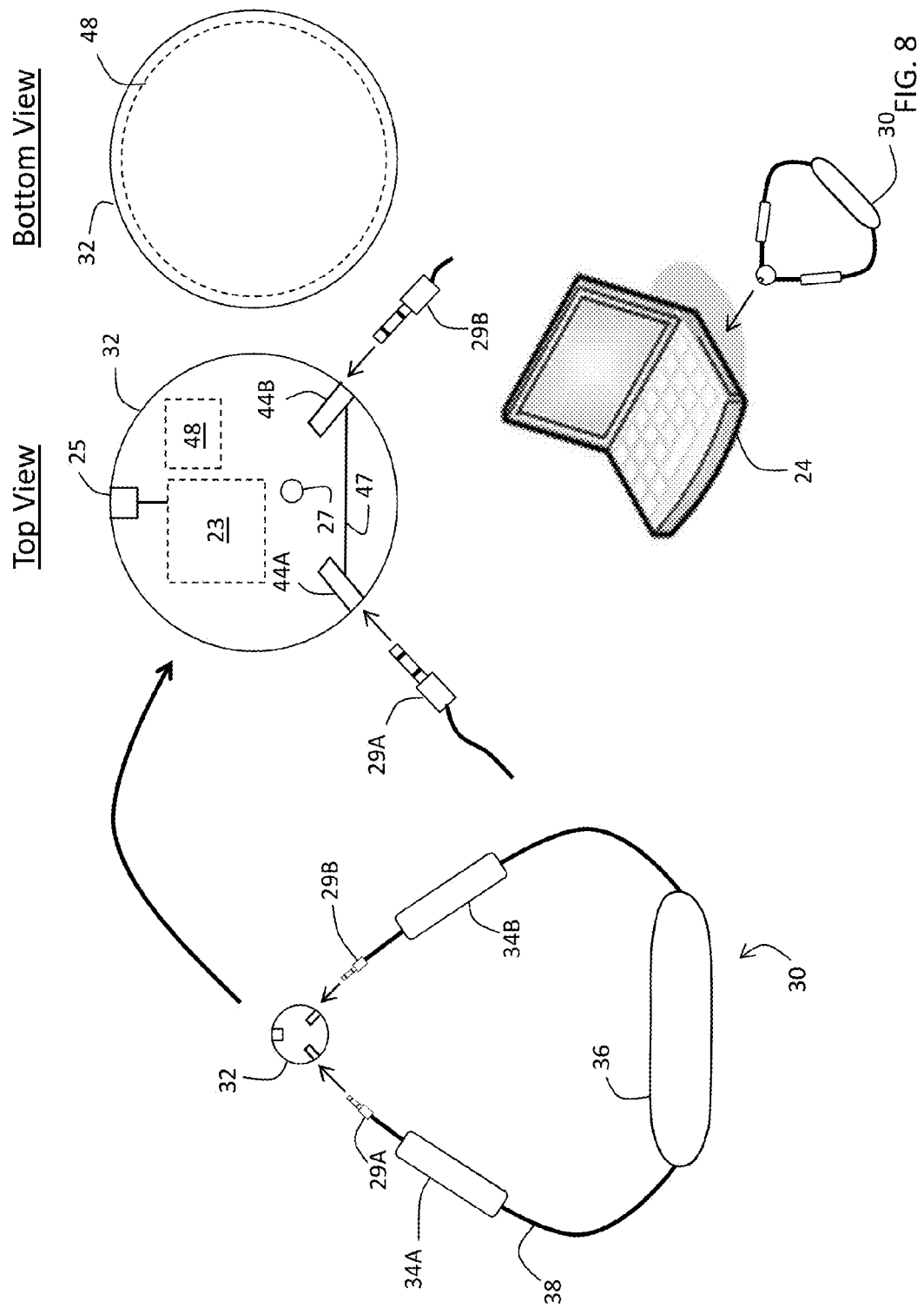
FIG. 8 shows a mechanical drawing of the sensor of FIG. 1 and its associated battery and data-transfer systems.

Referring back to FIG. 1, and in more detail in FIG. 8, a battery module 32 featuring a rechargeable Li:ion battery 48 connects at two points to the cable 38 using a pair of connectors 29A, 29B. During use, the connectors 29A, 29B plug into a pair of mated connectors 44A, 44B that securely hold the terminal ends of the cable 38 so that the sensor 30 can be comfortably and securely draped around the patient's neck. Importantly, when both connectors 29A, 29B are plugged into the battery module 32, the circuit within the sensor 30 is completed, and the battery module 32 supplies power to the electronics module 36 to drive the above-mentioned measurements. The connectors 29A, 29B terminating the cable can also be disconnected from the connectors 44A, 44B on the battery module 32 so that this component can be replaced without removing the sensor 30 from the patient's neck. Replacing the battery module 32 in this manner means the sensor 30 can be worn for extended periods of time without having to remove it from the patient. In general, the connectors 29A, 29B can take a variety of forms: they can be flat, multi-pin connectors, such as those shown in FIG. 1, or stereo-jack type connectors, such as those shown in FIG. 8, that quickly plug into a female adaptor. Both sets of connectors 29A, 29B, 44A, 44B may also include a magnetic coupling so that they easily snap together, thereby making the sensor easy to apply. Typically an LED 27 on the battery module indicates that this is the case, and that the system is operational. When the battery within battery module 32 is nearly drained, the LED 27 indicates this particular state (e.g., by changing color, or blinking periodically). This prompts a user to unplug the battery module 32 from the two connectors, plug it into a recharge circuit (not shown in the figure), and replace it with a fresh battery module as described above. Also contained within the battery module is a flash memory card 23 for storing numerical and waveform data, and a micro-USB port 25 that connects to the flash memory card 23 for transferring data to a remote computer 24. Typically the micro-USB port 25 is also used for recharging the battery when the sensor is removed from the patient. In embodiments, these components can also be moved to the electronics module 36.

As is clear from FIG. 1, the neck-worn cable 38 serves four distinct purposes: 1) it transfers power from the battery module 32 to the electronics module 36; 2) it ports signals from the electrode patches 35, 37 to the impedance and ECG circuits; 3) it ensures consistent electrode placement for the impedance and ECG measurements to reduce measurement errors; and 4) it distributes the various electronics components and thus allows the sensor to be comfortably worn around the patient's neck. Typically each arm of the cable 38 will have 6 wires: 2 for the impedance electrodes 41A, 41C, 1 for the ECG electrode, and 3 to pass signals from the electronics module to electrical components within the battery module (flash memory card 23, LED 27). These wires can be included as discrete elements, a flex circuit, or, as described above, a flexible cable.

FIG. 2 shows the above-described sensor 30 worn around the neck of a patient 10. As described above, the sensor 30 includes an electronics module 36 worn on the back of the patient's neck, a battery module 32 in the front, and electrode holders 34A, 34B that connect to a cable 38 draped around the neck that make impedance and ECG measurements.

Figure 3:
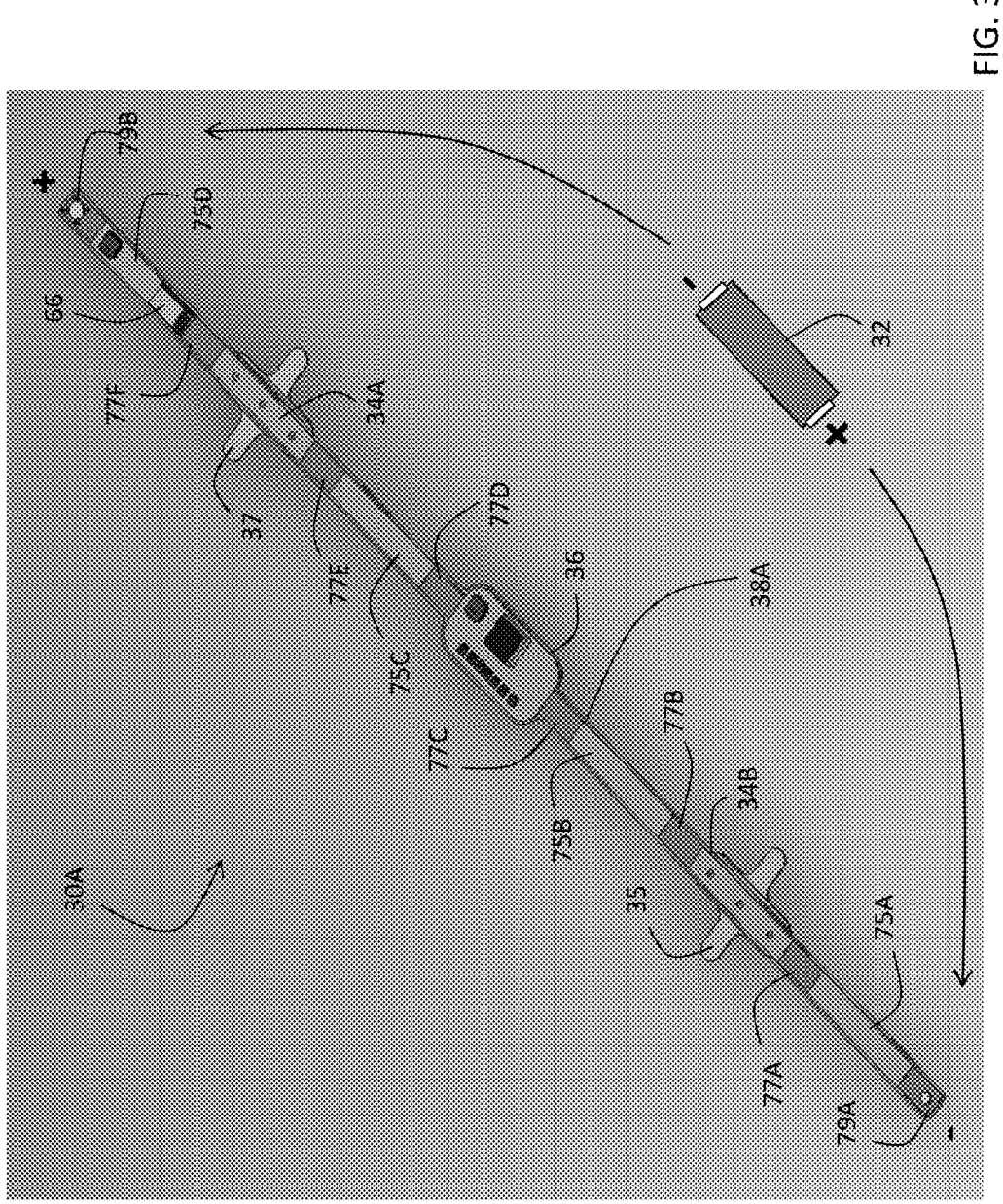
FIG. 3 shows a three-dimensional image of an embodiment of the necklace-shaped sensor that features alternating flexible and non-flexible circuit boards integrated directly into a cable configured to drape around the patient's neck.

FIG. 3 shows an alternate sensor 30A, also featuring a necklace form factor described above, only all circuit elements used for the TBI and ECG measurements, along with those for digital signal processing and wireless data transmission, are integrated directly into the cable 38A that wraps around the patient's neck. In this design, the sensor's cable includes all circuit elements, which are typically distributed on an alternating combination of rigid, fiberglass circuit boards and flexible Kapton® (DuPont USA) circuit boards. Typically these circuit boards are potted with a protective material, such as silicone rubber, to increase patient comfort and protect the underlying electronics. The battery for this design can be integrated directly into the cable, or connect to the cable with a conventional connector, such as a stereo-jack connector, micro-USB connector, or magnetic interface.

Referring again to FIG. 3, the necklace sensor 30A features alternating segments of multi-layer fiberglass-based circuit boards 75A-D and single-layer flexible, Kapton® tape-based conducting elements 77A-F. Typically the Kapton® tape-based conducting elements 77A-F are sandwiched between layers of the fiberglass-based circuit boards to ensure that they don't easily detach. To electrically connect the appropriate elements in the circuit boards 75A-D and conducting elements 77A-F, a clear hole can be drilled in the circuit board 75A-D and then filled with conductive solder. Typically the length of segments of the circuit boards 75A-D and conductive elements 77A-F is no more than a few centimeters; this ensures that the sensor 30A comfortably drapes around the patient's neck like a conventional necklace. Also dispersed along the span of the cable 38A are a pair of 3-snap electrode holders 34A, 34B that receive corresponding 3-part conductive electrode patches 35, 37; an electronics module 36 positioned near the center of the cable 38A so that, during use, it is positioned near the back of the patient's neck; and a wireless transmission module 66 similar to that described above. The cable 38A is terminated with a pair of magnetically active leads 79A, 79B (+/−) that are attracted to opposing, magnetically active poles of a battery module 32. During use, when the sensor 30A is draped around the patient's neck, the battery module 32 is drawn to the magnetically active leads 79A, 79B and automatically snaps into place. An electrical connection is established that provides power to all the electrical elements described above. The battery module 32 is simply snapped off of the magnetically active leads 79A, 79B and replaced when it is running low on power. Such a design is meant to optimize battery replacement for patients with compromised dexterity, e.g. elderly patients with CHF.

FIG. 9 depicts how the sensor 30 shown in FIG. 1 is designed to facilitate remote monitoring of a patient 10. As shown in the top portion of the figure, after the sensor 30 measures the patient, it automatically transmits data through its internal Bluetooth wireless transmitter to the patient's cellular telephone 20. In this case, the cellular telephone 20 preferably runs a downloadable software application that accesses the phone's internal Bluetooth® drivers, and includes a simple patient-oriented application that renders data on the phone's screen. From there, using its internal modem, the cellular telephone 20 transmits data to an IP address associated with a computer server 22. The computer server 22, in turn, renders a web-based system that displays data for clinicians at a hospital, medical clinic, nursing facility, or eldercare facility. The web-based system may show ECG and TBI waveforms, trended numerical data, the patient's medical history, along with their demographic information. A clinician viewing the web-based system may, for example, analyze the data and then call the patient 10 and have them adjust their medications or diet. Alternatively, as shown in the lower half of the figure, the sensor 30 can automatically transmit data through Bluetooth® to a personal computer 24, which then uses a wired or wireless Internet connection to transmit data to the computer server 22. Here, the personal computer 24 runs a custom software program to download data from the sensor 22, display it for the patient in an easy-to-understand format, and then forward it to the computer server for a relatively complex analysis as described above. In yet another embodiment, the sensor 30 is directly plugged into the personal computer 24 through a USB connection, and data are downloaded using a wired connection and forwarded to the computer server 22 as described above.

FIG. 10 shows examples of user interfaces 90, 91, 92 that integrate with the above-mentioned systems and run on the cellular telephone 20, shown in this case as an iPhone® (Apple, Inc.). The user interfaces show information such as patient demographics (interface 90), patient-oriented messages (interface 91), and numerical vital signs and time-dependent waveforms (interface 92). The interfaces shown in the figures are designed for the patient. More screens, of course, can be added, and similar interfaces (preferably with more technical detail) can be designed for the actual clinician. The interfaces can also be used to render operational reports, such as those generated with the system of FIG. 19. Reports showing similar data are, of course, possible.

FIG. 4 shows competing systems in the prior art that make impedance measurements from a patient. For example, the system 5 on the left is typically wheeled on a cart, and connects to electrodes worn on the patient's body through a collection of wired leads. It typically measures CO, SV, ECG, and HR in a medical clinic or hospital. The system 6 shown in the middle features an electronics box that can be carried by the patient or attached to their clothing, and, like the system 5 shown on the left, connects to the patient with a collection of wired leads to measure CO and SV. It is typically used for ambulatory patients. And the system 7 shown on the right is a single patch worn on the patient's chest that measures fluids in the thoracic cavity. This too is typically used for ambulatory patients.

FIG. 5 indicates in more detail how the above-described sensor measures TBI waveforms and CO/SV values from a patient. As described above, 3-part electrode patches 35, 37 within the neck-worn sensor attach to the patient's chest. Ideally, each patch 35, 37 attaches just below the collarbone near the patient's left and right arms. During a measurement, the impedance circuit injects a high-frequency, low-amperage current (I) through outer electrodes 31C, 41C. Typically the modulation frequency is about 70 kHz, and the current is about 4 mA. The current injected by each electrode 31C, 41C is out of phase by 180°. It encounters static (i.e. time-independent) resistance from components such as bone, skin, and other tissue in the patient's chest. Additionally, blood conducts the current to some extent, and thus blood ejected from the left ventricle of the heart into the aorta offers a dynamic (i.e. time-dependent) resistance. The aorta is the largest artery passing blood out of the heart, and thus it has a dominant impact on the dynamic resistance; other vessels, such as the superior vena cava, will contribute in a minimal way to the dynamic resistance.

Inner electrodes 31A, 41A measure a time-dependent voltage (V) that varies with resistance (R) encountered by the injected current (I). This relationship is based on Ohm's Law (V=I×R). During a measurement, the time-dependent voltage is filtered by the impedance circuit, and ultimately measured with an analog-to-digital converter within the electronics module. This voltage is then processed to calculate SV with an equation such as that shown below in Eq. 3, which is Sramek-Bernstein equation, or a mathematical variation thereof. Historically parameters extracted from TBI signals are fed into the equation, shown below, which is based on a volumetric expansion model taken from the aortic artery:

$$SV = \delta \frac{L^3}{4.25} \frac{(dZ(t)/dt)_{max}}{Z_0} LVET \qquad (3)$$

In Eq. 3, Z(t) represents the TBI waveform, δ represents compensation for body mass index, $Z_0$ is the base impedance, L is estimated from the distance separating the current-injecting and voltage-measuring electrodes on the thorax, and LVET is the left ventricular ejection time, which can be determined from the TBI waveform, or from the HR using an equation called 'Weissler's Regression', shown below in Eq. 4, that estimates LVET from HR:

$$LVET = -0.0017 \times HR + 0.413 \qquad (4)$$

Weissler's Regression allows LVET, to be estimated from HR determined from the ECG waveform. This equation and several mathematical derivatives, along with the parameters shown in Eq. 3, are described in detail in the following reference, the contents of which are incorporated herein by reference: Bernstein, *Impedance cardiography: Pulsatile blood flow and the biophysical and electrodynamic basis for the stroke volume equations*; J Electr Bioimp; 1: 2-17 (2010). Both the Sramek-Bernstein Equation and an earlier derivative of this, called the Kubicek Equation, feature a 'static component', $Z_0$, and a 'dynamic component', $\Delta Z(t)$, which relates to LVET and a $(dZ/dt)_{max}/Z_o$ value, calculated from the derivative of the raw TBI signal, $\Delta Z(t)$. These equations assume that $(dZ(t)/dt)_{max}/Z_o$ represents a radial velocity (with units of $\Omega/s$) of blood due to volume expansion of the aorta.

Figure 11:
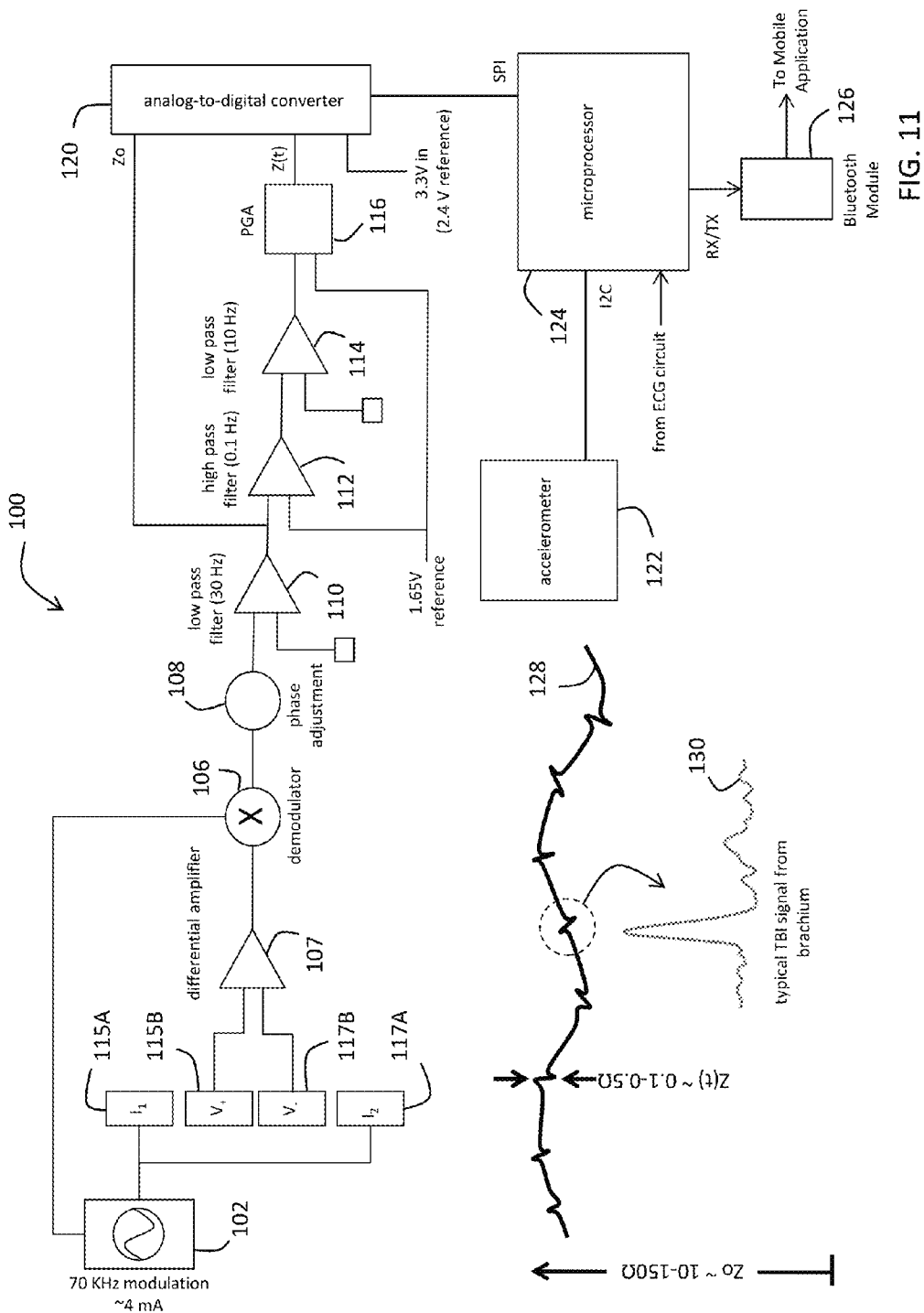
FIG. 11 shows a schematic drawing of an electrical circuit used within the sensor of FIG. 1 to make the impedance measurement.

FIG. 11 shows an analog circuit 100 that performs the impedance measurement according to the invention. The figure shows just one embodiment of the circuit 100; similar electrical results can be achieved using a design and collection of electrical components that differ from those shown in the figure.

The circuit 100 features a first electrode 115A that injects a high-frequency, low-amperage current ($I_1$) into the patient's brachium. This serves as the current source. Typically a current pump 102 provides the modulated current, with the modulation frequency typically being between 50-100 KHz, and the current magnitude being between 0.1 and 10 mA. Preferably the current pump 102 supplies current with a magnitude of 4 mA that is modulated at 70 kHz through the first electrode 115A. A second electrode 117A injects an identical current ($I_2$) that is out of phase from $I_1$ by 180°.

A pair of electrodes 115B, 117B measure the time-dependent voltage encountered by the propagating current. These electrodes are indicated in the figure as V+ and V−. As described above, using Ohm's law ($V=I\times R$), the measured voltage divided by the magnitude of the injected current yields a time-dependent resistance to ac (i.e. impedance) that relates to blood flow in the aortic artery. As shown by the waveform 128 in the figure, the time-dependent resistance features a slowly varying dc offset, characterized by Zo, that indicates the baseline impedance encountered by the injected current; for TBI this will depend, for example, on the amount of fat, bone, muscle, and blood volume in the chest of a given patient. Zo, which typically has a value between about 10 and 150Ω, is also influenced by low-frequency, time-dependent processes such as respiration. Such processes affect the inherent capacitance near the chest region that TBI measures, and are manifested in the waveform by low-frequency undulations, such as those shown in the waveform 128. A relatively small (typically 0.1-0.5Ω) AC component, $\Delta Z(t)$, lies on top of Zo and is attributed to changes in resistance caused by the heartbeat-induced blood that propagates in the brachial artery, as described in detail above. $\Delta Z(t)$ is processed with a high-pass filter to form a TBI signal that features a collection of individual pulses 130 that are ultimately processed to ultimately determine SV and CO.

Voltage signals measured by the first electrode 115B (V+) and the second electrode 117B (V−) feed into a differential amplifier 107 to form a single, differential voltage signal which is modulated according to the modulation frequency (e.g. 70 kHz) of the current pump 102. From there, the signal flows to a demodulator 106, which also receives a carrier frequency from the current pump 102 to selectively extract signal components that only correspond to the TBI measurement. The collective function of the differential amplifier 107 and demodulator 106 can be accomplished with many different circuits aimed at extracting weak signals, like the TBI signal, from noise. For example, these components can be combined to form a 'lock-in amplifier' that selectively amplifies signal components occurring at a well-defined carrier frequency. Or the signal and carrier frequencies can be deconvoluted in much the same way as that used in conventional AM radio using a circuit that features one or more diodes. The phase of the demodulated signal may also be adjusted with a phase-adjusting component 108 during the amplification process. In one embodiment, the ADS 1298 family of chipsets marketed by Texas Instruments may be used for this application. This chipset features fully integrated analog front ends for both ECG and impedance pneumography. The latter measurement is performed with components for digital differential amplification, demodulation, and phase adjustment, such as those used for the TBI measurement, that are integrated directly into the chipset.

Once the TBI signal is extracted, it flows to a series of analog filters 110, 112, 114 within the circuit 100 that remove extraneous noise from the Zo and $\Delta Z(t)$ signals. The first low-pass filter 110 (30 Hz) removes any high-frequency noise components (e.g. power line components at 60 Hz) that may corrupt the signal. Part of this signal that passes through this filter 110, which represents Zo, is ported directly to a channel in an analog-to-digital converter 120. The remaining part of the signal feeds into a high-pass filter 112 (0.1 Hz) that passes high-frequency signal components responsible for the shape of individual TBI pulses 130. This signal then passes through a final low-pass filter 114 (10 Hz) to further remove any high-frequency noise. Finally, the filtered signal passes through a programmable gain amplifier (PGA) 116, which, using a 1.65V reference, amplifies the resultant signal with a computer-controlled gain. The amplified signal represents $\Delta Z(t)$, and is ported to a separate channel of the analog-to-digital converter 120, where it is digitized alongside of Zo. The analog-to-digital converter and PGA are integrated directly into the ADS 1298 chipset described above. The chipset can simultaneously digitize waveforms such as Zo and $\Delta Z(t)$ with 24-bit resolution and sampling rates (e.g. 500 Hz) that are suitable for physiological waveforms. Thus, in theory, this one chipset can perform the function of the differential amplifier 107, demodulator 108, PGA 116, and analog-to-digital converter 120. Reliance of just a single chipset to perform these multiple functions ultimately reduces both size and power consumption of the TBI circuit 100.

Digitized Zo and $\Delta Z(t)$ waveforms are received by a microprocessor 124 through a conventional digital interface, such as a SPI or I2C interface. Algorithms for converting the waveforms into actual measurements of SV and CO are performed by the microprocessor 124. The microprocessor 124 also receives digital motion-related waveforms from an on-board accelerometer, and processes these to determine parameters such as the degree/magnitude of motion, frequency of motion, posture, and activity level.

Figure 12:
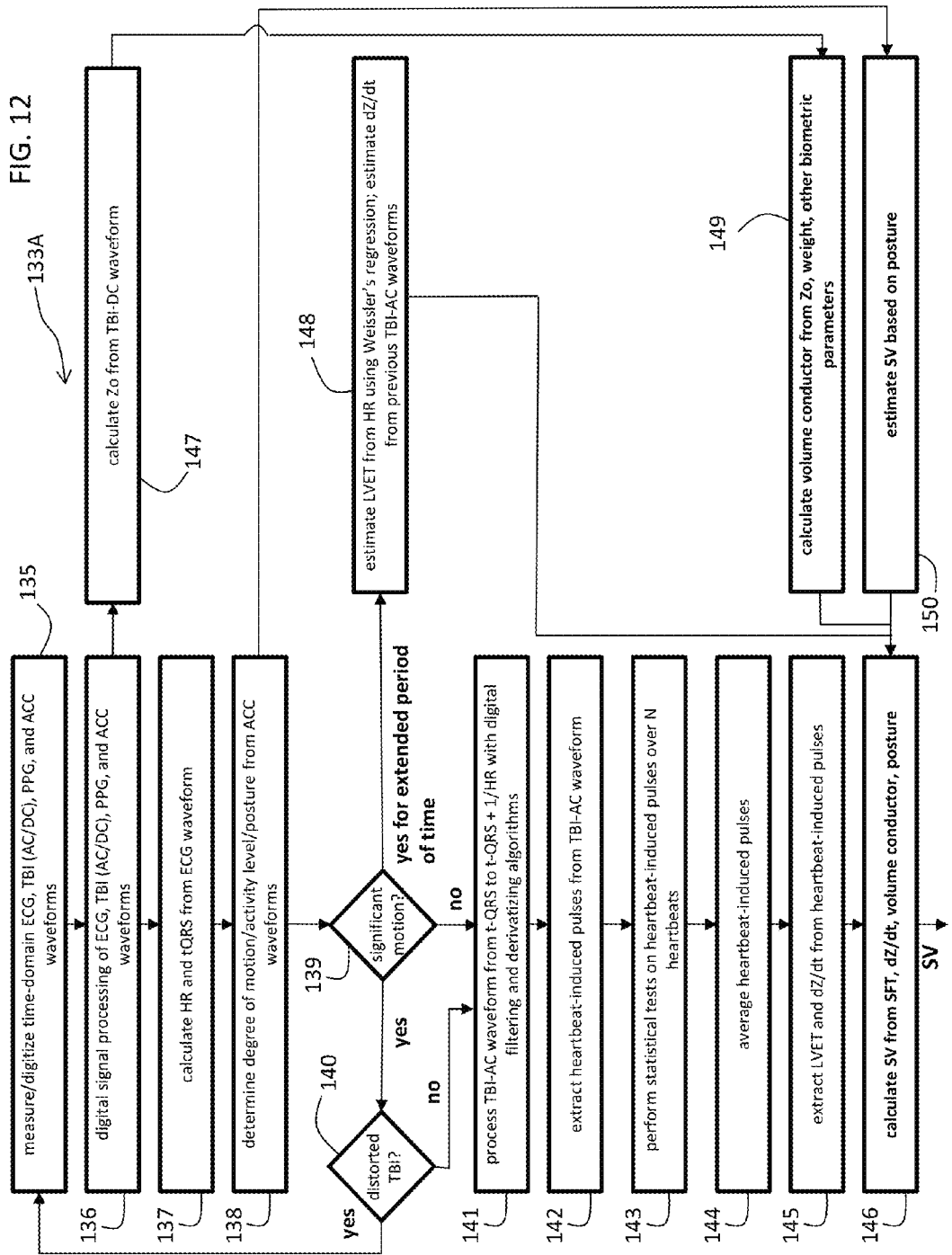
FIG. 12 shows a flow chart of an algorithm used to calculate SV during periods of motion.

FIG. 12 shows a flow chart of an algorithm 133A that functions using compiled computer code that operates, e.g., on the microprocessor 124 shown in FIG. 6. The algorithm 133A is used to measure TBI waveforms in the presence of motion. The compiled computer code is loaded in memory associated with the microprocessor, and is run each time a TBI measurement is converted into a numerical value for CO and SV. The microprocessor typically runs an embedded real-time operating system. The compiled computer code is typically written in a language such as C, C++, Java, or assembly language. Each step 135-150 in the algorithm 133A is typically carried out by a function or calculation included in the compiled computer code.

Physiological data similar to that generated with the sensor described above is shown in FIGS. 13-19. As shown in the top portion of FIG. 13, the TBI waveform is a time-dependent signal, with different components of the signal corresponding to unique physiological events. For example, the baseline of the TBI waveform corresponds to the relative fluid level in the patient's thoracic cavity. This parameter typically increases for patients entering into heart failure. Data shown in the figure correspond to a patient that was initially in an upright position. Other than the rapid time-dependent oscillations, which are described in more detail below, the average baseline is relatively constant. The patient is then rapidly inverted, resulting in the drop in baseline shown at point 201. In this case, conductive bodily fluid pools in the patient's thoracic cavity, thus increasing the conductivity of current injected during the impedance measurement, and consequently decreasing the resistance (i.e. impedance) measured near the chest. A short time later, the patient is reverted to their original, standing-up position. Fluid drains quickly from their thoracic cavity as indicated by point 203, thus reducing conductivity and increasing impedance. FIG. 12 indicates that these small changes in thoracic fluid result in clear, measurable changes in impedance, as shown in the TBI waveform. For patients with CHF, the change in fluid level will be more gradual, likely happening over several days. Making one-time measurements with the sensor over this period can monitor such changes. A gradual increase in fluid levels, monitored with the end-to-end system shown in FIG. 8, will gradually decrease thoracic impedance levels measured with the sensor described herein. Automated computer algorithms, or technicians working in a call center and trained to interpret data, can alert a supervising clinician to the patient's status. The clinician can respond to the patient's increase in fluid levels by ordering a change in diet (e.g. to reduce sodium content), exercise, or by altering the medication (e.g. by increasing a dose of a diuretic, such as Lasix).

Figure 13:
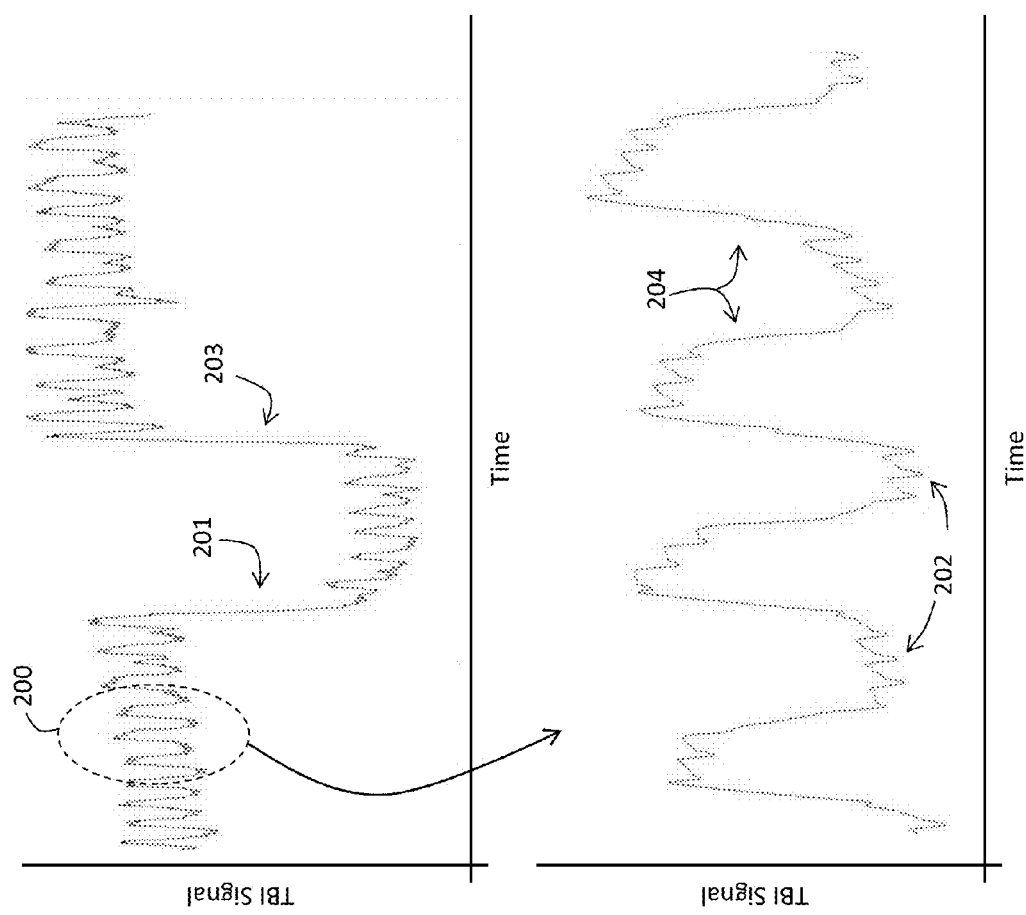
FIG. 13 shows graphs of time-dependent impedance waveforms measured with a prototype of the sensor of FIG. 1.

The bottom portion of FIG. 13 shows how respiratory rate, CO, and SV can be extracted from the TBI waveform. The low-frequency oscillations in the waveforms, as shown by points 204, indicate breathing-induced changes in thoracic impedance. Thus they can be analyzed (e.g. counted with a simple beatpicking algorithm) to accurately determine the patient's respiratory rate. Such a determination is important during the onset of heart failure, as an increase in respiration rate often indicates a gradual lowering of oxygen-containing blood being pumped by the patient's heart. These data, combined with data describing thoracic fluid levels, can be used to identify a patient entering into heart failure. The relatively high-frequency oscillations in the plot, shown by point 202, indicate cardiac pulses. Here, blood pumped by the heart into the aorta, which because of its hemoglobin is a good electrical conductor, results in a rapid, time-dependent change in the patient's thoracic impedance. This change is indicated by a collection of heartbeat-induced pulses that are analyzed as described below to determine SV. From there, SV and CO are calculated using Eqs. 3 and 4, as described above.

Figure 14:
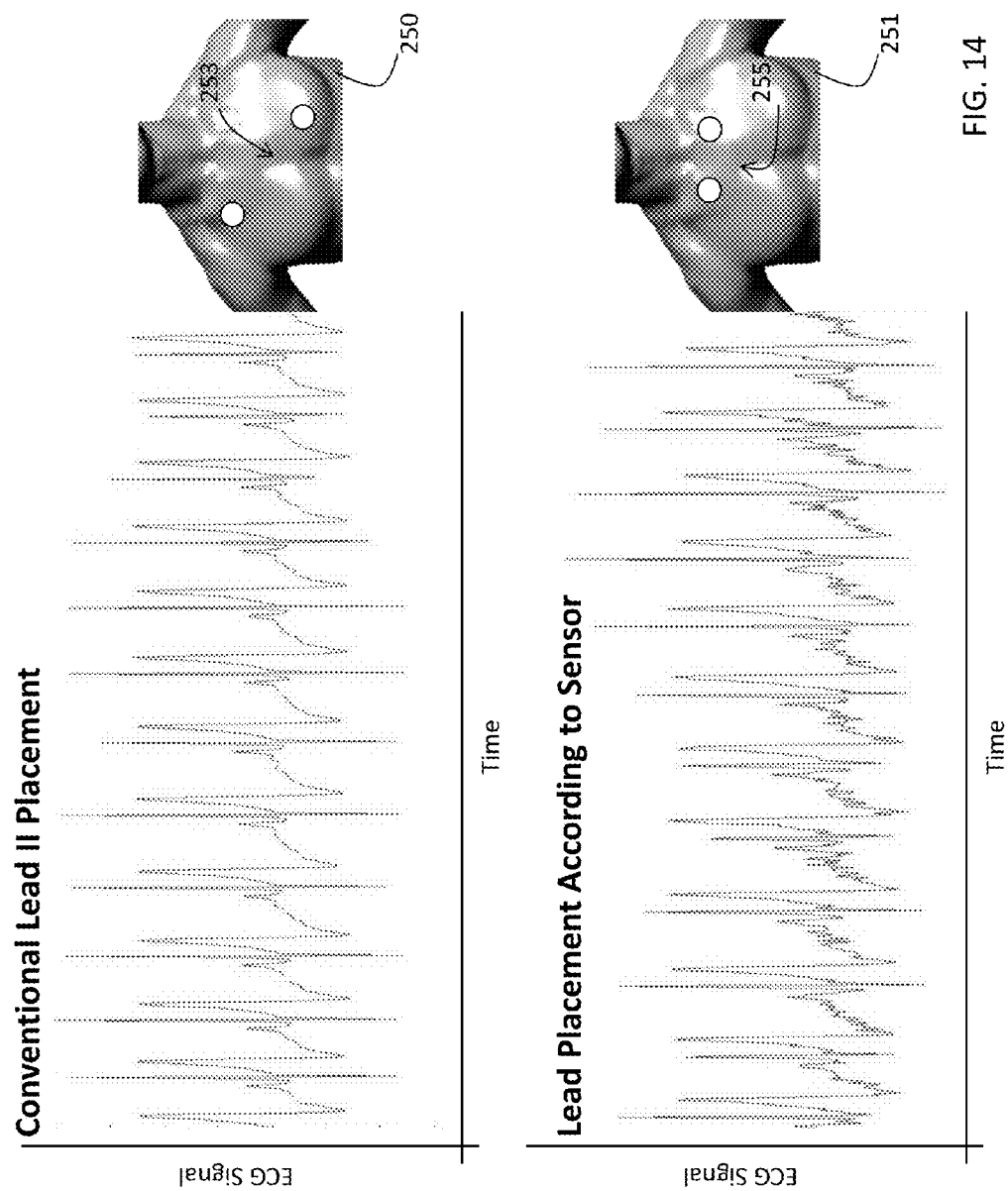
FIG. 14 shows graphs of time-dependent ECG waveforms, measured with the prototype of the sensor of FIG. 1, from two different locations on the patient's thoracic cavity.

Somewhat surprisingly, as shown in FIG. 14, ECG waveforms can be accurately measured near the neck with the sensor described herein. The top portion of the figure shows an ECG waveform measured with a conventional Lead II placement 253, as indicated by the torso 250 in the figure. Here, a first electrode is placed on the right-hand side of the torso 250, about 5 cm below the collarbone, and a second electrode on the left-hand side of the torso 250, about 15 cm above the waist. In contrast, the bottom portion of the figure shows the lead placement according to the necklace-shaped sensor. A torso 251 in the figure indicates the placement of electrodes 255 for this measurement. Comparing the two waveforms indicates a nearly identical morphology for this particular patient. The waveform measured by the necklace sensor has a relatively low signal-to-noise ratio, likely because the sensing electrodes are relatively close together, thus resulting in a weaker signal. But any high-frequency noise in this case can be easily removed using a simple digital low-pass filter (cutoff around 40 Hz) or even simple techniques based on, e.g., a running average. HR and associated cardiac arrhythmias can then be easily determined through analysis of the well-known QRS complexes in the figure.

Figure 15:
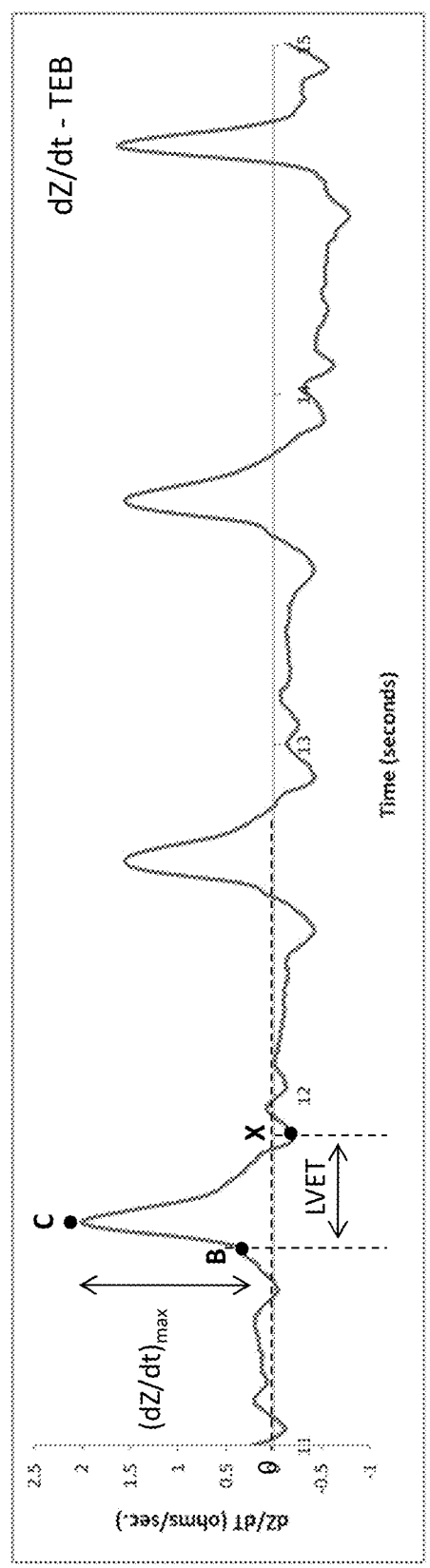
FIG. 15 shows a mathematical derivative of a time-dependent TBI waveform.
Figure 16:
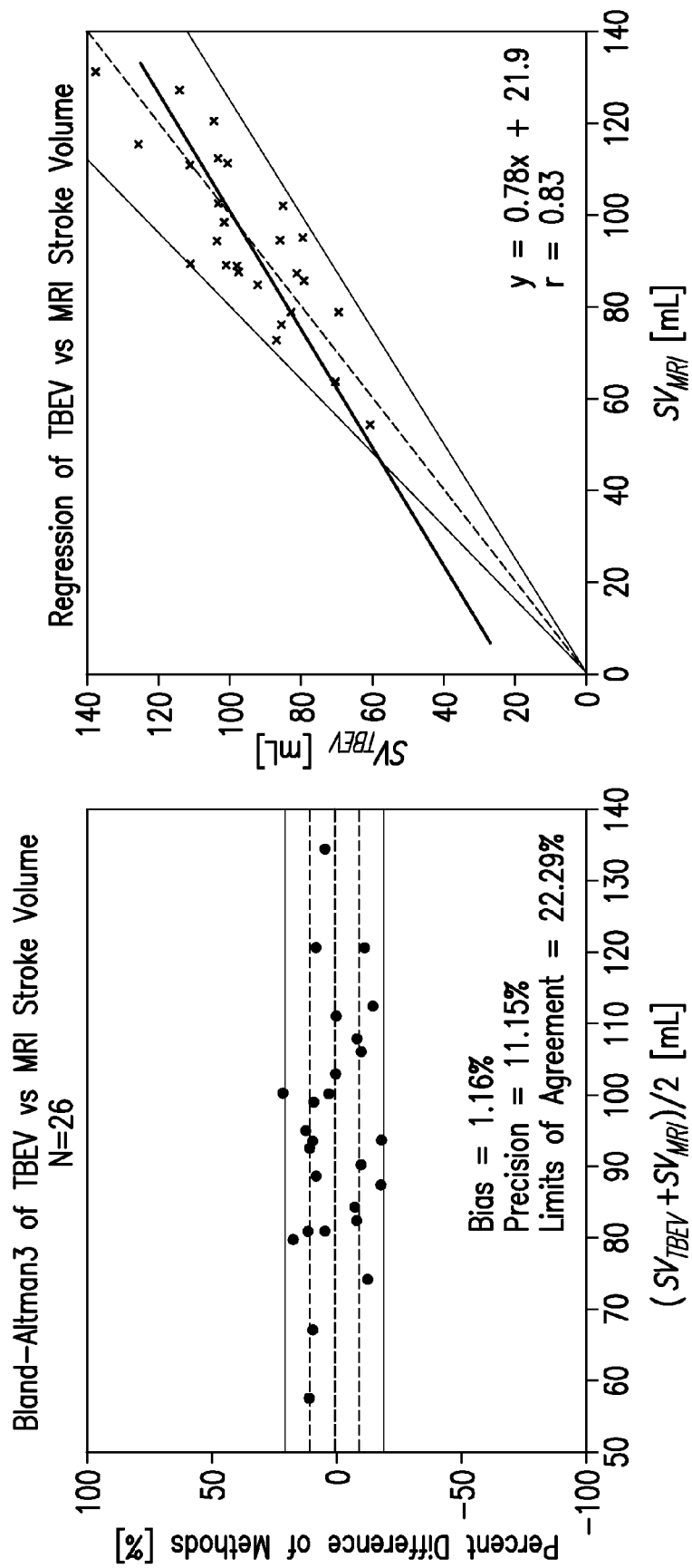
FIG. 16 shows Bland-Altman (left) and correlation (right) graphs of SV measured with a technique similar to TBI and magnetic resonance imaging (MRI) during a clinical trial.

FIG. 15 indicates how LVET is extracted from the derivatized TBI waveform. The derivatized ICG waveform features consecutive pulses, each characterized by three points: a 'B' point on the pulse's upswing indicating opening of the aortic valve; an X point on the pulse's nadir indicating closing of the aortic valve; and a 'C' point on its maximum value indicating the maximum slope of the $\Delta Z(t)$ pulse's upswing, which is equivalent to $(dZ/dt)_{max}$. LVET is typically calculated from the time differential between the B and X points. However, due to the subtle nature of these fiducial markers, even low levels of noise in the waveforms can make them difficult to determine. Ultimately such noise adds errors to the calculated LVET and resulting SV.

The analysis described above was used in a formal clinical study to test accuracy of determining SV using a technique similar to TBI and Eq. 3 above, compared to SV determined using MRI. Correlation and Bland-Altman plots are shown, respectively, in the right and left-hand sides of FIG. 16. The shaded gray area in the plots indicates the inherent errors associated with conventional Doppler/ultrasound measurements, which are about +/−20%. In total 26 subjects (14M, 12W) with ages ranging from 21-80 were measured for this study, and correlations for all of these subjects fell within the error of the MRI measurements.

Figure 17:
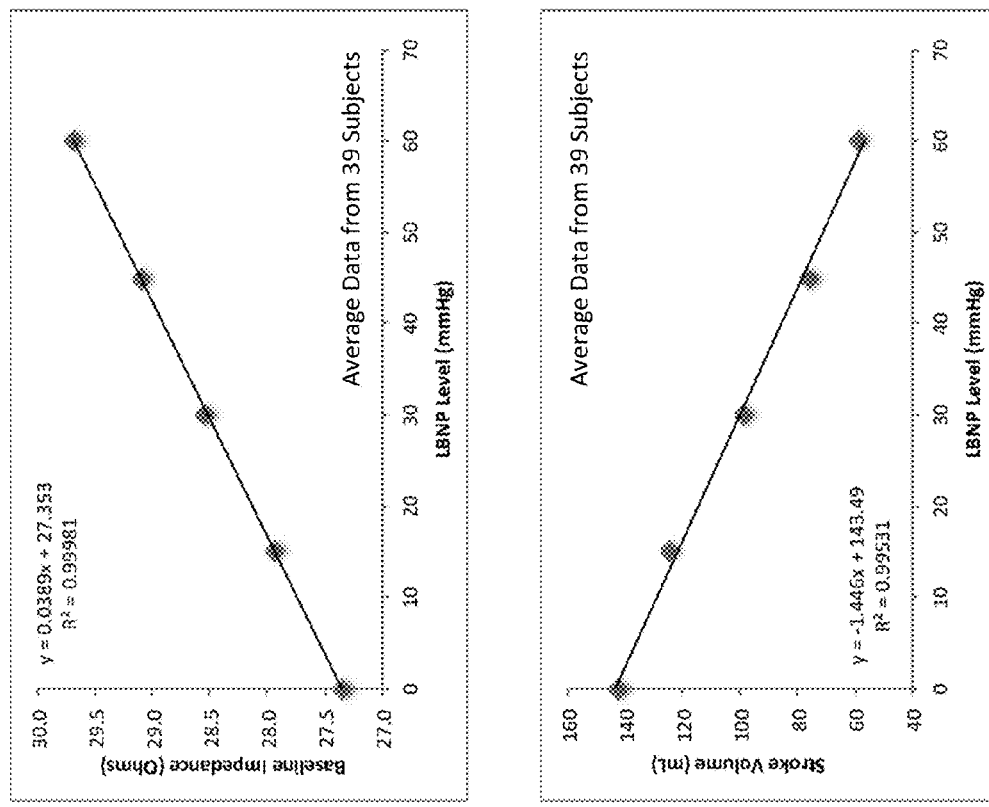
FIG. 17 shows correlation graphs of data, averaged from 39 subjects, of baseline impedance (top) and SV (bottom) compared to lower body negative pressure (LBNP) level, which is an experimental technique for simulating CHF.
Figure 18:
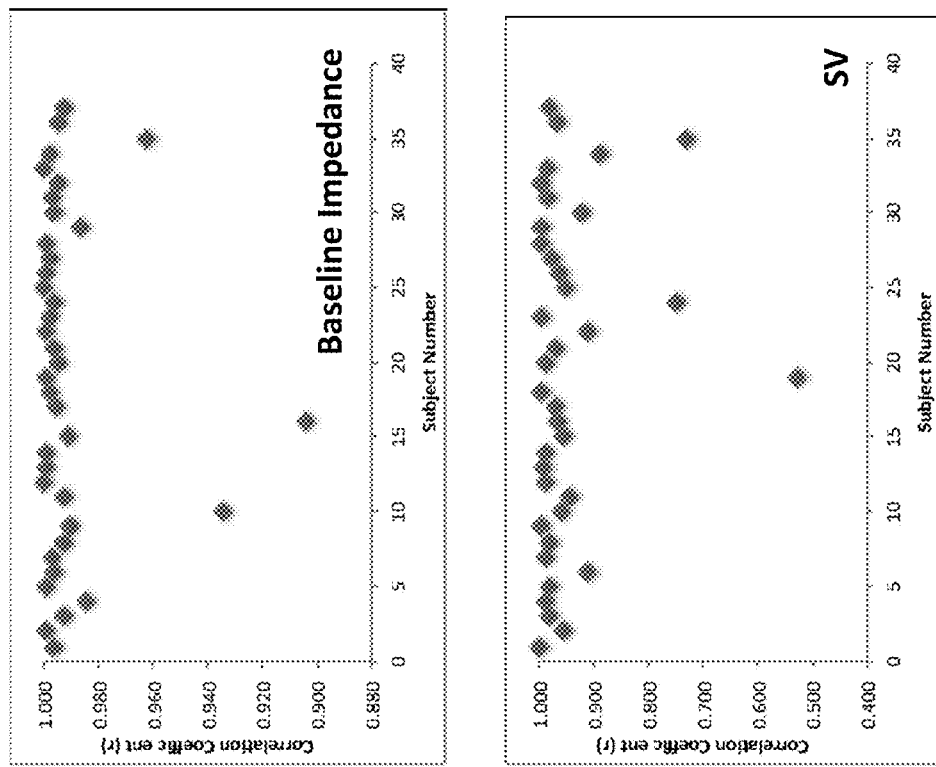
FIG. 18 shows graphs of Pearson's correlation coefficients (r), measured from each of the subjects used to generate the data for FIG. 17, describing the relationship of baseline impedance and SV to LBNP.

FIGS. 17 and 18 show data collected from a sensor operating an impedance measurement, similar to that described above, on patients undergoing an experimental protocol called 'lower body negative pressure' (LBNP). During LBNP, a patient is inserted into a vacuum chamber up to their waist. The vacuum chamber then applies a gradually increasing vacuum to the patient's lower extremities, thereby essentially sucking blood and other fluids from the patient's thoracic cavity into the legs and waist. In this way, LBNP works in an opposite manner to CHF, i.e. it gradually reduces thoracic fluids, as opposed to increasing them. Traditionally, LBNP is used to simulate hemorrhage in patients because it essentially removes blood from the body's major organs. Typically during hemorrhage SV is decreased. Such a reduction can also occur during CHF, and thus LBNP is an ideal experimental technique for inducing changes in two properties—thoracic fluid level and SV—that also undergo a time-dependent change during CHF.

FIG. 17 shows pooled results from 39 subjects undergoing a gradual increase in LBNP from 0 mmHg (i.e. no change from ambient) to a vacuum of 60 mmHg (corresponding to a loss of blood of about 2 L). The data shown in this figure are averaged over all 39 subjects, and impedance waveforms similar to those described above were measured from the thoracic cavity and analyzed to determine SV and thoracic fluid level. As shown in the top portion of the figure, the change in baseline impedance correlates in a linear manner with the LBNP level, with the agreement between these parameters (Pearson's correlation coefficient $r^2$=0.9998) being extremely high. Here, vacuum applied during LBNP gradually removes conductive fluids from the thoracic cavity, thus decreasing conductivity and increasing baseline impedance. Similarly, the relationship between LBNP level and SV shown in the bottom half of the plot is also linear, with the slope going in the opposite direction as that for the impedance/LBNP correlation. In this case increasing LBNP removes blood from the patient's thoracic cavity, thus reducing their effective blood volume (called 'pre-load') and essentially simulating hemorrhage. During hemorrhage, the body is trained to reduce blood flow by decreasing the amount of blood pumped by the heart (the SV) to preserve perfusion of the internal organs. Thus, it is expected that increasing LBNP will systematically decrease SV, which is exactly what is shown in the lower half of FIG. 17. The correlation for this relationship is also quite high, with $r^2=0.99531$.

In conclusion, the results shown in FIG. 17 indicate that two parameters that change with the onset of CHF—thoracic fluid level and SV—can be accurately measured with an impedance-based technique, such as that deployed with the sensor described herein.

The data shown in FIG. 17 are averaged over all 39 subjects, while the individual correlation coefficient for each subject for the above-described measurements are shown in FIG. 18. As is clear from these data, 36 out of 39 subjects show a correlation between LBNP level (representing a proxy for fluid level, as described above) and baseline impedance characterized by $r>0.98$, which is extremely high. Similarly, 36 out of 39 subjects show a correlation between LBNP level and SV characterized by $r>0.9$. Both of these plots indicate that the parameters measured by impedance measurements show promise for being an accurate physiological monitor.

Figure 19:
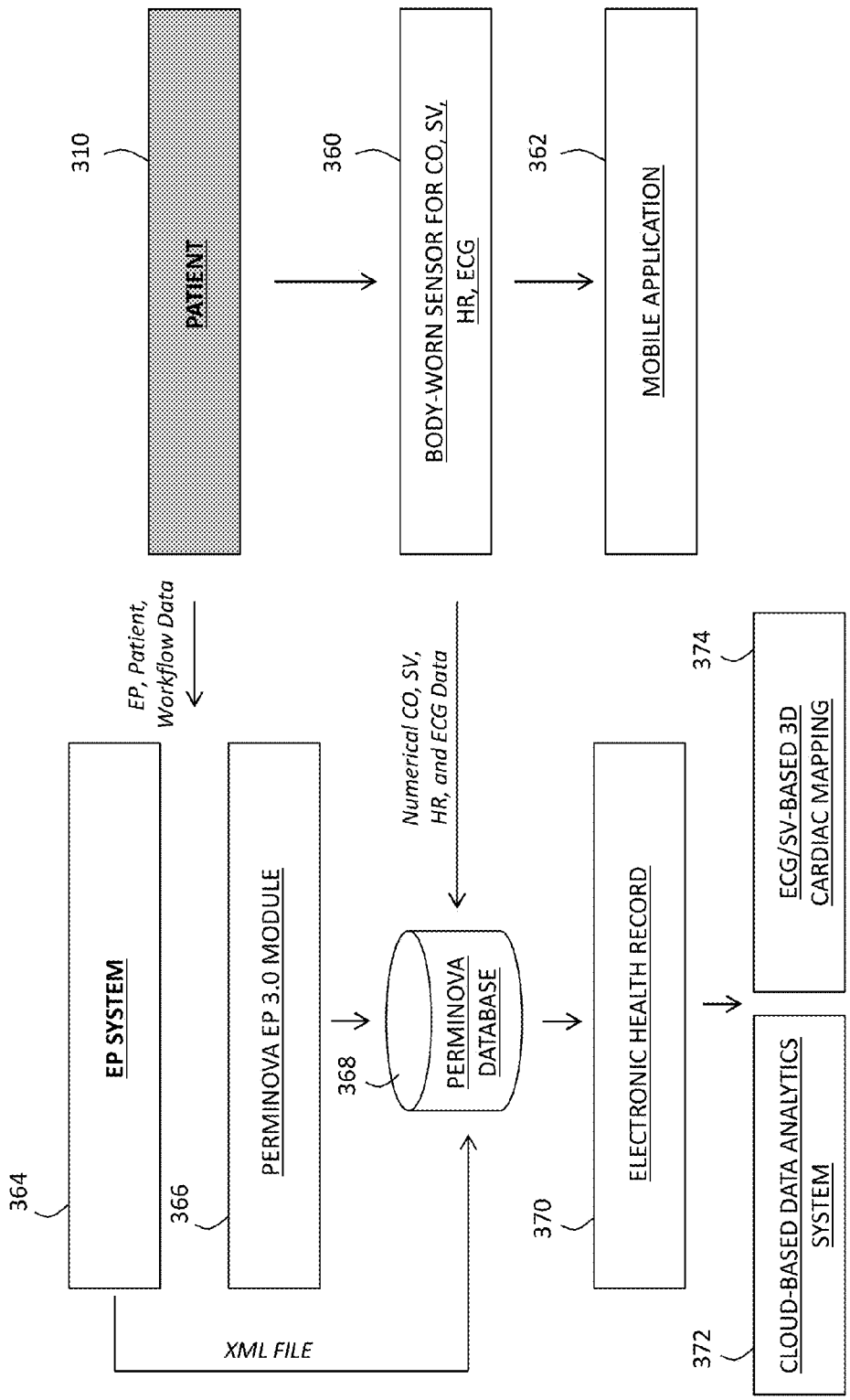
FIG. 19 shows a schematic drawing of a system that includes the sensor of FIG. 1 and a web-based software system used to monitor an electrophysiology (EP) procedure.

FIG. 19 shows how the above-described sensor integrates into a web-based system for treating a patient with a process called electrophysiology (EP). EP is used, for example, to treat patients suffering from arrhythmias whom may not be candidates for an implanted device, such as a pacemaker. In embodiments, the EP system shown in the figure is similar to that described in the co-pending patent application entitled INTERNET-BASED SYSTEM FOR COLLECTING AND ANALYZING DATA BEFORE, DURING, AND AFTER A CARDIOVASCULAR PROCEDURE (U.S. Ser. No. 61/711, 096; filed Oct. 8, 2012), the contents of which are incorporated herein by reference.

As shown in the figure, a patient 310 is treated with an EP System 364, such as the Bard LabLink™ Data Interface, that synchronizes and integrates 3D mapping systems (e.g. the Carto® 3 System) with EP Recording Systems (e.g. the LabSystem™ PRO EP Recording System). The EP System 364 allows selection of stimulation channels from either the recording or mapping system, and merges patient demographics, 3D image snapshots and cardiovascular event data, e.g. waveforms measured with internal electrodes, refractory periods, and ablation information. During an EP procedure, the EP System 364 outputs an XML file that includes these data, encoded as either numerical values or waveforms. The XML file passes to a Database 368, where an XML parsing engine decodes it before the data elements are stored in specific fields, as described in more detail below.

An EP Module 366 also provides data for the Database 368. The EP Module 366 is preferably a system that collects information during the EP procedure, such as data describing: i) patient demographics; ii) vital signs; iii) supplies used during the EP procedure; iv) billing information; and v) clinician information.

During the EP procedure, data from the EP System 364 and EP Module 366 flow from the Database 368 into the patient's Electronic Health Record 370, which is usually associated with an enterprise-level, medical-records software system deployed at the hospital, such as that provided by Epic or Cerner. Data from the Electronic Health Record 370 can be further processed by a Cloud-Based Data Analytics System 372, which is similar to that described in the above-mentioned patent application, the contents of which have been previously incorporated herein by reference. As described in this patent application, the Cloud-Based Data Analytics System 372 processes physiological, procedural, and operational data collected before, during, and after the EP procedure to generate custom reports and perform numerical studies. The above-referenced patent application includes several examples of how the Cloud-Based Data Analytics System 372 can process physiological data to evaluate the patient and the EP procedure overall. Additionally, a Cardiac Mapping System 374 processes CO, SV, HR, and ECG data measured by a Body-Worn Sensor 60 to generate 3D images of the patient's heart. A Mobile Application 362, similar to that shown in FIG. 10, also receives data wirelessly from the Body-Worn Sensor 360, described in detail below, thereby allowing a clinician to remotely monitor the patient 310.

Systems similar to that described above can also be used for other cardiac procedures conducted in other areas of the hospital, such as the catheterization laboratory, medical clinic, or vascular analysis laboratory. In these applications, data other than HR and ECG waveforms may be analyzed using techniques similar to those described above. Data used in these examples includes medical images (such as those measured using MRI or Doppler/ultrasound), all vital signs, hemodynamic properties such as cardiac output and stroke volume, tissue perfusion, pH, hematocrit, and parameters determined with laboratory studies.

In other embodiments, signals from the wireless transceiver within the sensor can be analyzed (e.g. triangulated) to determine the patient's location. In this case, a computer operating at a central monitoring station, such as that used at a hospital, can perform triangulation. Alternative, the patient's cellular telephone can be used for this purpose. In still other embodiments, the sensor can include a more conventional location system, such as a global positioning system (GPS). In this case the GPS and its associated antenna are typically included on a rigid circuit board that connects to the data-processing system within the sensor.

In still other embodiments, the necklace-shaped sensor can be augmented to include other physiological sensors, such as a pulse oximeter or blood pressure monitor. For example, the pulse oximetry circuit can be included on a rigid circuit board within the necklace, and then can connect to an ear-worn oximetry sensor. The geometry of the sensor described herein, and its proximity to the patient's ear, makes this measurement possible. For blood pressure, a parameter called pulse transit time, which is measured between a fiducial point on the ECG waveform (e.g. the QRS complex) and a fiducial point (e.g. an onset) of a TBI pulse (such as the C point shown in FIG. 15), correlates inversely to blood pressure. Thus measuring this parameter and calibrating it with a conventional measurement of blood pressure, such as that done with an oscillometric cuff, can yield a continuous, non-invasive measurement of blood pressure.

Still other embodiments are within the scope of the following claims.

What is claimed is:

1. A sensor for measuring both impedance and ECG waveforms and configured to be worn around a patient's neck, comprising:
(i) a first electrode patch module comprising at least first and second electrodes and a backing supporting the at least first and second electrodes and providing an adhesive surface; and a second electrode patch module comprising at least third and fourth electrodes and a backing supporting the at least third and fourth electrodes and providing an adhesive surface, wherein the first and second electrode patch modules configured to be spatially separate and adhesively positioned on opposite sides of the medial axis of the patient's chest at approximately shoulder level below the collarbone;

(ii) a harness configured in a necklace form factor, the harness comprising:

an electronics module configured to be positioned near the patient's neck, the electronics module comprising a digital processing system comprising a microprocessor and an analog-to-digital converter and a wireless transceiver;

a first sensor module configured reversibly mate to the first electrode patch module and to electrically connect the first and second electrodes to the electronics module via a first cable segment, and to operably connect a first electrical connector to the electronics module via a second cable segment;

a second sensor module configured reversibly mate to the second electrode patch module and to electrically connect the third and fourth electrodes to the electronics module via a third cable segment, and to operably connect a second electrical connector to the electronics module via a fourth cable segment; and a battery module configured to reversibly mate to the first electrical connector and to the second electrical connector to electrically connect the battery module to the electronics module, wherein the electronics module, the first sensor module, the second sensor module, the first cable segment, the second cable segment, the third cable segment, the fourth cable segment, the first electrical connector, and the second electrical connector are of unitary construction;

the electronics module, the battery module, the first sensor module, and the second sensor module form an analog ECG circuit when the first sensor module is in electrical contact with the first electrode and the second sensor module is in electrical contact with the third electrode, the ECG circuit configured to generate an analog ECG waveform;

the electronics module, the battery module, the first sensor module, and the second sensor module form an analog impedance circuit when the first sensor module is in electrical contact with the first and second electrodes and the second sensor module is in electrical contact with the third and fourth electrodes, the impedance circuit configured to generate an analog impedance waveform; and the digital processing system is configured to receive and process the analog ECG and impedance waveforms and to generate therefrom digital ECG and impedance waveforms, to determine therefrom on a continuous basis a heart rate (HR) value, a stroke volume (SV) value, a cardiac output (CO) value, and a cardiac rhythm status for the patient and to transmit the HR value, the SV value, the CO value, and the cardiac rhythm status to an external computer.

2. The sensor of claim 1, wherein the harness comprises a plurality of wires that electrically connect the electronics module, the battery module, the first sensor module, and the second sensor module.

3. The system of claim 1, wherein the harness comprises a flexible circuit that electrically connects the electronics module, the battery module, the first sensor module, and the second sensor module.

4. The system of claim 1, wherein the harness comprises at least two non-flexible circuit boards connected to each other with a flexible circuit board.

5. The system of claim 4, wherein one of the non-flexible circuit boards comprises the ECG circuit, and the other comprises the digital processing system.

6. The system of claim 4, wherein one of the non-flexible circuit boards comprises the impedance circuit, and the other comprises the digital processing system.

7. The system of claim 1, wherein the second electrode is a current-injecting electrode, the fourth electrode is a current-injecting electrode, the first electrode is a voltage-measuring electrode, and the third electrode is a voltage-measuring electrode.

8. The system of claim 1, wherein the wireless transceiver is one of a Bluetooth® transceiver and an 802.11-based transceiver.

9. The system of claim 1, further comprising a USB connector in electrical contact with a flash memory system.

10. The system of claim 9, wherein the cable comprises the USB connector.

* * * * *